(12) United States Patent
Thiel et al.

(10) Patent No.: US 6,846,649 B1
(45) Date of Patent: Jan. 25, 2005

(54) RECOMBINANT HUMAN MANNAN-BINDING LECTIN

(76) Inventors: Steffen Thiel, Villadsensvej 3, DK-8240 Risskov (DK); Jens Christian Jensenius, Finsens Alle 28, DK-5230 Odense (DK); Thomas Vorup Jensen, Faborggade 14, DK-8000 Arhus (DK)

( * ) Notice: Subject to any disclaimer, the term of this patent is extended or adjusted under 35 U.S.C. 154(b) by 0 days.

(21) Appl. No.: 09/568,143

(22) Filed: May 10, 2000

(30) Foreign Application Priority Data

May 14, 1999 (DK) .......................................... 1999 00668
Oct. 20, 1999 (DK) .......................................... 1999 01508

(51) Int. Cl.$^7$ .......................... C07H 1/06; C07K 17/00; C12P 21/02
(52) U.S. Cl. ...................... 435/69.1; 530/412; 530/413; 530/396; 536/23.5
(58) Field of Search .............................. 435/69.1, 69.6, 435/252.3; 536/23.1, 23.5; 530/396, 412, 413

(56) References Cited

U.S. PATENT DOCUMENTS 5,112,952 A   5/1992  Mallia et al.
5,270,199 A  12/1993  Ezekowitz

FOREIGN PATENT DOCUMENTS

EP  0856580   8/1998
WO  9910001   3/1999
WO  9964453  12/1999

OTHER PUBLICATIONS

Stryer et al, in Biochemistry, third edition, W. H. Freeman and Company, New York, 1988, p. 112.*
Tabona et al., Immunology 85(1): 153–9, May 1995; PTO 892.*
Davies, et al., "Mannose–Binding Protein Gene Polymorphism in Systemic Lupus Erythematosus," *Arthritis & Rheumatism* 38: 110–114 (1995).
Drickamer, et al., "Mannose–binding Proteins Isolated from Rat Liver Contain Carbohydrates–recognition Domains Linked to Collagenous Tails," *The Journal of Biological Chemistry* 261(15):6878–6887 (1986).
Christiansen, et al., "Mannan–Binding Lectin Deficiency is Associated with Unexplained Recurrent Miscarriage," *Scand. J. Immunol.* 49:193–196 (1999).
van Emmerik, "Binding of Mannan–Binding Protein to Various Bacterial Pathogens of Meningitis," *Clin. Exp. Immunol.* 97:411–416 (1994).
Garred, et al., "Mannan–Binding Lectin in the Sub–Saharan HIV and Tuberculosis Epidemics," *Scand. J. Immunol.* 46:204–208 (1997).
Garred, et al., "Susceptibility to HIV Infection and Progression of AIDS in Relation to Variant Alleles of Mannose–Binding Lectin," *The Lancet* 349:236–240 (1997).

Guo, e t al., "The Human Ortholog of Rhesus Mannose–binding Protein–A Gene is an Expressed Pseudogene that Localizes to Chromosome 10," *Mammalian Genome* 9:246–249 (1998).
Hanahan, "Studies on Transformation of *Escherichia coli* with Plasmids," *J. Mol. Biol.* 166:557–580 (1983).
Hartshorn, et al., "Conglutinin Acts as an Opsonin for Influenza A Viruses," *The Journal of Immunology* 151(11):6265–6273 (1993).
Haurum, et al., "Complement Activation Upon Binding of Mannan–binding Protein to HIV Envelope Glycoproteins," *AIDS* 7:1307–1313 (1993).
Hemmilä, et al., "Di– and Tetracarboxylate Derivatives of Pyridines, Bipyridines and Terpyridines as Luminogenic Reagents for Time–resolved Fluorometric Determination of Terbium and Dysprosium," *Journal of Biochemical and Biophysical Methods* 26:283–290 (1993).
Holmskov, et al., "Purification and Characterization of Bovine Mannan–binding Protein," *Glycobiology* 3(2):147–153 (1993).
Holmskow, et al., "Collectins: Collagenous C–type Lectins of the Innate Immune Defense System," *Immunology Today* 15(2):67–74 (1994).
Abstract of Huang, et al., "Stable Expression of Anti–HPV 16 E7–Ribozyme in CV–1 Cell Lines," *Chin. J. Biotechnol.* 12(4):215–220 (1996).
Iobst, et al., "Binding of Sugar Ligands to $Ca^{2+}$–dependent Animal Lectins," *The Journal of Biological Chemistry* 269(22):15505–15511 (1994).
Ip, et al., "Association of Systemic Lupus Erythematosus with Promoter Polymorphisms of the Mannose–Binding Lectin Gene," *Arthritis & Rheumatism* 41(9):1663–1668 (1998).
Janeway, et al., "Immunobiology," $4^{th}$ Edition. Churchill Livingston, Edinburg (1999).
Madsen, et al., "Interplay Between Promoter and Structural Gene Variants Control Basal Serum Level of Manham Binding Protein," *Journal of Immunology* 155:3013–3020 (1995).
Malhotra, et al., "Binding of Human Collectins (SP–A and MBP) to Influenza Virus," *Biochem. J.* 304:455–461 (1994).

(List continued on next page.)

*Primary Examiner*—Christina Chan
*Assistant Examiner*—Phuong Huynh
(74) *Attorney, Agent, or Firm*—Iver P. Cooper

(57) ABSTRACT

The present invention relates to methods of producing and/or isolating MBL compositions. In particular the invention relates to methods of producing and/or isolating novel recombinant human MBL preparations with high similarity to natural human MBL. The MBL preparations may be used in compositions, medicaments and in methods for treatment of conditions such as those related to immunosuppressive conditions and/or to conditions of MBL deficiencies including latent conditions. Conditions of deficiencies of Mannan-Binding Lectin (MBL) are associated with increased susceptibility to infections.

30 Claims, 5 Drawing Sheets

OTHER PUBLICATIONS

Matsushita, et al., "Activation of the Classical Complement Pathway by Mannose–Binding Protein in Association with a Novel Cls–like Serine Protease," *J. Exp. Med.* 176:1497–1502 (1992).

Matsushita, et al., "The Gly–54—Asp Allelic Form of Human Mannose–binding Protein (MBP) fails to Bind MBP–associated Serine Protease," *Biochem. J.* 311:1021–1023 (1995).

Mizuno, et al., "Isolation and Characterization of a Mannan–binding Protein from Rat Liver," *The Journal of Biological Chemistry* 256(9):4247–4252 (1981).

Mogues, et al., "Characterization of Two Mannose–binding Protein cDNAs from Rhesus Monkey (*Macaca mulatta*): Structure and Evolutionary Implications," *Glycobiology* 6:543–550 (1996).

Makrides, et al., "Components of Vectors for Gene Transfer and Expression in Mammalian Cells," *Protein Expression and Purification* 17:183–202 (1999).

Nakajima, et al., "Characterization of the Carbohydrate Fragments Obtained from *Saccharomyces cerevisiae* Mannan by Alkaline Degradation," *The Journal of Biological Chemistry* 249(23):7679–7684 (1974).

Ng., et al., "Structural Analysis of Monosaccharide Recognition by Rat Liver Mannose–binding Protein," *The Journal of Biological Chemistry* 271(2):663–674 (1996).

Nielsen, et al., "The Level of the Serum Opsonin, Mannan–binding Protein in HIV–1 Antibody–Positive Patients," *Clin. Exp. Immunol.* 100:219–222 (1995).

Ohta, et al., "The Mechanism of Carbohydrate–mediated Complement Activation by the Serum Mannan–Binding Protein," *The Journal of Biological Chemistry* 265(4):1980–1984 (1990).

Ohtani, et al., "High–level and Effective Production of Human Mannan–binding Lectin (MBL) in Chinese Hamster Ovary (CHO) Cells," *Journal of Immunological Methods* 222:135–144 (1999).

Oka, et al., "Isolation and Characterization of Mannan–Binding Proteins from Chicken Liver," *Archives of Biochemistry and Biophysics* 241:95–105 (1985).

Oka, et al., "Isolation and Characterization of Two Distinct Mannan–Binding Proteins from Rat Serum," *Archives of Biochemistry and Biophysics* 260(1):257–266 (1988).

Pastinen, et al., "Contribution of the CCR5 and MBL Genes to Susceptibility to HIV Type 1 Infection in the Finnish Population," *AIDS Research and Human Retroviruses* 14(8):695–698 (1988).

Reddy, et al., "Assembly, Sorting, and Exit of Oligomeric Proteins from the Endoplasmic Reticulum," *BIOESSAYS* 20(7):546–554 (1998).

Sastry, et al., "Exon Structure Reveals its Evolutionary Relationship to a Human Pulmonary Surfactant Gene and Localization to Chromosome 10," *J. Exp. Med.* 170:1175–1189 (1989).

Sato, et al., "Molecular Characterization of a Novel Serine Protease Involved in Activation of the Complement System by Mannose–binding Protein," *International Immunology* 6(4):665–669 (1993).

Schweinle, et al., "Truncated Forms of Mannose–binding Protein Multimerize and Bind to Mannose–rich *Salmonella montevideo* but Fail to Activate Complement in Vitro," *The Journal of Biological Chemistry* 268(1):364–370 (1993).

Ji, et al., "Activation of the C4 and C2 Components of Complement by a Proteinase in SerumBacterial Factor, Ra Reactive Factor," *The Journal of Immunology* 150(2):571–578 (1993).

Kawai, et al., "Molecular and Biological Characterization of Rabbit Mannan–Binding Protein (MBP)," *Glycobiology* 8(3):237–244 (1998).

Kawasaki, et al., "Isolation and Characterization of a Mannan–Binding Protein from Rabbit Liver," *Biochemical and Biophysical Research Communications*, 81(3):1018–1024 (1978).

Kilpatrick, et al., "Mannan Binding Protein in sera Positive for Rheumatoid Factor," *British Journal of Rheumatology* 36:207–209 (1997).

Kuhlma, et al., "The Human Mannose–Binding Protein Functions as an Opsonin," *The Journal of Experimental Medicine*, 169:173301745 (1989).

Kurata, et al., "Role of the Collagen–like Domain of the Human Serum Mannan–Binding Protein in the Activation of Complement and The Secretion of this Lectin," *Biochemical and Biophysical Research Communications* 191(3):1204–1210 (1993).

Abstract of Kurata, et al., "Structure and Function of Mannin–Binding Proteins Isolated from Human Liver and Serum," *Journal of Biochemistry* 115(6):1148–1154 (1994).

Lau, et al., "Mannose–Binding Protein in Chinese Patients with Systemic Lupus Erythematosus," *Arthritis & Rheumatism* 39(4):706–708 (1996).

Laursen, et al., "Collectin in a Non–Mammalian Species: Isolation and Characterization of Mannan–Binding Protein (MBP) from Chicken Serum," *Glycobiology* 5(6):553–561 (1995).

Laursen, et al., "Cloning and Sequencing of a cDNA Encoding Chicken Mannan–Binding Lectin (MBL) and Comparison with Mammalian Analogues," *Immunology* 93:421–430 (1998).

Law, et al., "Complement," $2^{nd}$ Edition, IRL Press, Oxford (1995).

Lipscombe, et al., "Identical Point Mutation Leading to Low Levels of Mannose Binding Protein and Poor C3b Mediated Opsonisation in Chinese and Caucasian Populations," *Immunology Letters* 32:253–258 (1992).

Lipscombe, et al., "High Frequencies in African and non–African Populations of Independent Mutations in the Mannose Binding Protein Gene," *Human Molecular Genetics* 1(9):709–715 (1992).

Lipscombe, et al, "Distinct Physicochemical Characteristics of Human Mannose Binding Protein Expressed by Individuals of Differing Genotype," *Immunology* 85:660–667 (1995).

Lu, et al., "Binding of the Pentamer/Hexamer Forms of Mannan–Binding Protein to Zymosan Activates the Proenzyme $Cl_{r2}Cl_{s2}$ Complex, of the Classical Pathway of Complement, without Involvement of Clq," *The Journal of Immunology* 144(6):2287–2294 (1990).

Ma, et al., "Structural and Functional Roles of the Amino–Terminal Region and Collagen–Like Domain of Human Serum Mannan–Binding Protein," *Biochemistry and Molecular Biology International* 40(5):965–974 (1996).

Ma, et al., "Functional Expression of Human Mannan–Binding Proteins (MBPs) in Human Hepatoma Cell Lines Infected by Recombinant Vaccinia Virus: Post–Translational Modification, Molecular Assembly, and Differentiation of Serum and Liver MBP," *J. Biochem.* 122(4):111–119 (1997).

Ma, et al., "Antitumor Activity f Mannan–Binding Protein in vivo as Revealed by a Virus Expression System: Mannan–Binding Protein–dependent Cell–Mediated Cytotoxicity," *Proc. Natl. Acad. Sci.* 96:371–375 (1999).

Madsen, et al., "A New Frequent Allele is the Missing Link in the Structural Polymorphism of the Human Mannan–Binding Protein," *Immunogenetics* 40:37–44 (1994).

Sheriff, et al., "Human Mannose–Binding Protein Carbohydrate Recognition Domain Trimerizes Through a Triple α–Helical Coiled–Coil," *Structural Biology* 1(11):789–794 (1994).

Soothill, et al., "Defective Opsonization," *Archives of Disease in Childhood* 51:91–99 (1976).

Stover, et al., "Two Constituents of the Initiation Complex of the Mannan–Binding Lectin Activation Pathway of Complement are Encoded by a Single Structural Gene," *Journal of Immunology* 162:3481–3490 (1999).

Sumiya, et al., "Molecular Basis of Opsonic Defect in Immunodeficient Children," *The Lancet* 337:1569–1570 (1991).

Super, et al., "Association of Low Levels of Mannan–Binding Protein with a Common Defect of Opsonisation," *The Lancet* ii:1236–1239 (1989).

Super, et al., "Distinct and Overlapping Functions al Allelic forms of Human Mannose Binding Protein," *Nature Genetics* 2:50–55 (1992).

Abstract of Tabona, et al., "Mannose binding Protein is Involved in First–line Host Defence: Evidence from Transgenic Mice," *Immunology* 85:153–159 (1995).

Takada, et al., "A New Member of the Cls Family of Complement Proteins Found in a Bactericidal Factor, Ra–Reactive Factor, in Human Serum," *Biochemical and Biophysical Research Communications* 196(2):1003–1009 (1993).

Takayama, et al., "A 100–kDa Protein in the C4–Activating Component of Ra–Reactive Factor is a New Serine Protease Having Module Organization Similar to C1r and C1s," *Journal of Immunology* 152:2308–2316 (1994).

Tan, et al., "The Genetics of Lupus," *Current Opinion in Rheumatology* 10:399–408 (1998).

Taylor, et al., "Structure and Evolutionary Origin of the Gene Encoding a Human Serum Mannose–binding Protein," Department of Biochemistry, Columbia University (1989(.

Thiel, et al., "A Second Serine Protease Associated with Mannan–biding Lectin that Activates Complement," *NATURE* 386:506–510 (1997).

Turner, "Mannose–binding Lectin: The Pluripotent Molecule of the Innate Immune System," *Immunology Today* 17(11):532–540 (1996).

Valdimarsson, et al., "Reconstruction of Opsonizing Activity by Infusion of Mannan–Binding Lectin (MBL) and MBL–Deficient Humans," *Scand. J. Immunol.* 48:116–123 (1998).

Vorup–Jensen, et al., "MASP–2, the C# Convertase Generating Protease of the MBLectin Complement Activating Pathway," *Immunobiology* 199:348–357 (1998).

Voss, et al., "Structural Comparison of Recombinant Pulmonary Surfactant Protein SP–A Derived from Two Human Coding Sequences: Implications for the Chain Composition of Natural Human SP–A," *Am. J. Respir. Cell Mol. Biol.* 4:88–94 (1991).

Weis, et al., "Structural of a C–type Mannose–binding Protein Complexed with an Oligosaccharide," *Nature* 360:127–134 (1992).

Weis, et al., "Trimeric Structure of a C–type Mannose–binding Protein," *Structure* 2(12): 1227–1240 (1994).

Garred, et al., "Increased Frequency of Homozygosity of Abnormal Mannan–binidng–protein Alleles in Patients with Suspected Immunodeficiency," *The Lancet* 346:941–943 (1995).

Summerfield, et al., "Association of Mutations in Mannose–binding Protein Gene with Childhood Infection in Consecutive Hospital Series," *BMJ* 314:1229–1232 (1997).

Garred, et al., "Association of Mannose–binding Lectin Gene Heterogeneity with Severity of Lung Disease and Survival in Cystic Fibrosis," *The Journal of Clinical Investigation* 104(4):431–437 (1999).

Gabolde, et al., "Association of Variant Alleles of Mannose Binding Lectin with Severity of Pulmonary Disease in Cystic Fibrosis: Cohort Study," *BMJ* 319:1166 (1999).

Hibberd, et al., "Association of Variants of the Gene for Mannose–binding Lectin with Susceptiblity to Meningococcal Disease," *The Lancet* 353:1049–1053 (1999).

Selander, et al., "Low Concentrations of Immunoglobulin G Antibodies to Salmonella Serogroup C in C2 Deficiency: Suggestion of a Mannan–Binding Lectin Pathway–Dependent Mechanism," *Scand. J. Immunol.* 50:555–561 (1999).

* cited by examiner

SEQUENCE LISTING

<160> NUMBER OF SEQ ID NOS: 3

<210> SEQ ID NO 1
<211> LENGTH: 248
<212> TYPE: PRT
<213> ORGANISM: Homo sapiens

<400> SEQUENCE: 1

```
Met Ser Leu Phe Pro Ser Pro Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
                35                  40                  45

Lys Asp Gly Arg Asp Gly Thr Lys Gly Glu Lys Gly Glu Pro Gly Gln
        50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 2
<211> LENGTH: 30
<212> TYPE: DNA
<213> ORGANISM: Artificial Sequence
<220> FEATURE:
<223> OTHER INFORMATION: synthetic

<400> SEQUENCE: 2
agattaacct tcctcgagtt ttctcacacc          30

<210> SEQ ID NO 3
<211> LENGTH: 29
<212> TYPE: DNA
<213> ORGANISM: Artificial Sequence
<220> FEATURE:
<223> OTHER INFORMATION: synthetic

```
<400> SEQUENCE: 3
taacggatcc actccaataa tacatacac                                              29
```

RECOMBINANT HUMAN MANNAN-BINDING LECTIN

The invention related to a process for preparing a composition comprising MBL, and treatment of diseases and disorders of the immune system comprising treatment of deficiencies within the immune defence system. In more particular, the invention concerns treatment of conditions or latent conditions of deficiencies of Mannan-Binding Lectin (MBL) which is associated with increased susceptibility to infections. The invention further concerns preparation of a novel expression construct encoding human MBL, a novel recombinant preparation of human MBL and furthermore it comprises use of this compound in methods for treatment of conditions such as those related to immunosuppressive chemotherapy and/or conditions of MBL deficiencies including latent conditions, i.e. not in a present need. The treatment are aimed at humans and at animals, in which the immune system appears to not similarly to the human immune system.

BACKGROUND OF THE INVENTION

The immune system comprises a complex array of cellular and molecular mechanisms which recognizes and targets pathogenic microorganism or the cells infected with them. Recently, MBL has gained great interest as an important part of the innate immune system, that is, the immune system which at time of birth is operational, in contrast to the adaptive immune defence which only during infancy obtains its full power of protecting the body (Janeway et al. 1999). Upon binding of carbohydrates of microbial surfaces, MBL mediates activation of the complement cascade, a series of enzymatic activation steps, which eventually label the target for destruction by phagocytosis or by lysis of the microorganism (Law & Reid, 1995). The complement system is being activated through at least three distinct pathways, designated the classical pathway, the alternative pathway, and the MBLectin pathway (Janeway et al., 1999). The classical pathway is initiated when complement factor 1 (C1) recognizes surface-bound immunoglobulin. The C1 complex is composed of two proteolytic enzymes, C1r and C1s, and a non-enzymatic part, C1q, which contains immunoglobulin-recognizing domains. C1q and MBL shares structural features, both molecules having a bouquet-like appearance when visualized by electron microscopy. Also, like C1q, MBL is found in complex with two proteolytic enzymes, the mannan-binding lectin associated proteases (MASP). The three pathways all generate a convertase of complement factor 3 (C3 convertase) bound to the surface of the activating surface, i.e., the targeted microbial pathogen. Conversion of C3 into surface bound C3b is pivotal in the process of eliminating the microbial pathogen by phagocytosis or lysis (Janeway et al., 1999).

Mannan-binding lectin (MBL), also named mannan-binding protein or mannose-binding protein (MBP), was first characterized in rabbits (Kawasaki at al., 1978). Mannan-binding lectin (MBL) belongs to a group of soluble $Ca^{2+}$-dependent (C-type) lectins containing a C-terminal carbohydrate recognition domain and a collagen-like region characterized by repeated triplet-motifs of glycine (Gly) followed by two non-glycine amino acids. Thus, MBL belongs to the group of collectins, i.e., C-type lectins with collagen-like regions, which in addition comprises the lung surfactant proteins A and D as well conglutinin and CL-43, these, however, only having been characterized in cattle (Holmskov et al., 1994). The human MBL protein is composed of up to 18 identical 32 kDa polypeptide chains (Lu et al., 1990), each comprising a short N-terminal segment of 21 amino acids including three cysteine residues, followed by 7 repeats of the collagenous motif Gly-X-Y interrupted by a Gin residues followed by another 12 Gly-X-Y repeats. A small 34 residue 'neck-region' joins the C-terminal $Ca^{2+}$-dependant lectin domain of 93 amino acids with the collagenous part of the molecule (Sastry et al., 1989). Three MBL polypeptide chains are joined in a MBL subunit. MBL consists of up to six 15 nm stalks of MBL subunits joined at the base of the bouquet. Later work characterized MBL in rodents (Mizuno et al., 1981; Oka et al., 1988), cattle (Holmskov et al., 1993a; Kawai et al., 1997), and chicken (Oka et al., 1985; Laursen et al., 1995; Laursen et al., 1998). In rodents (Drickamer et al., 1986) and rhesus monkeys (Mogues et al., 1996) two types of MBL genes have been identified, usually designated as A and C forms. In rats, an MBL 'B' pseudogene was found (Drickamer et al., 1985) and recently an MBL pseudogene was also cloned from the human genome, sequence analysis suggesting this to be remnants of a primate MBL-A gene (Guo et al., 1996). Human MBL was characterized by Kawasaki et al., in 1983. Only one active human MBL gene has been identified, comprising four exons with three intervening introns of the MBL gene spanning approximately 6 kb and is located at 10q11.2–q21 (Sastry et al., 1989; Taylor et al., 1989).

The collagenous regions of the three polypeptide chains combine to form a subunit which is stabilized covalently by disulphide bridges. Individual subunits are joined by disulphide bridges as well as by non-covalently interactions (Lu et al., 1990).

The position of these disulphide bridges has, however, not been fully resolved. SDS-PAGE analysis under non-reducing conditions of MBL shows bands with an apparent molecular weight (m.w.) larger than 200 kDa presumably representing blocks of 3, 4, 5 and even 6 assembled subunits (Lu et al., 1990).

The actual number of subunits in the natural human MOL protein has been controversial. Lipscombe et al, (1995) obtained data by use of ultracentrifugation suggesting 25% of human serum MBL to be made of 2–3 subunits and only a minor fraction reaching the size of 6 subunits. The relative quantification was carried out by densitometry of Western blots developed by chemiluminescence. Lower efficiency in transferring high molecular weight protein onto membranes compared to proteins of lower molecular weight make analysis through this methodology complicated. Lu et al. (1990) found by SDS-PAGE analysis of fractions from ion exchange chromatography that the predominant species of covalently linked MBL subunit chains consisted of tetramers while only pentameric or hexameric complexes activated complement. Gel permeation chromatography (GPC) analysis, in contrast, suggests that MBL is comparable in size with the C1 complex. GPC can be carried out under conditions which allow for a study of the importance of weak protein-protein interactions in the formation of MBL molecules and, in combination with standard MBL assay techniques, also allows for unbiased determination of the MBL content in the GPC fractions.

The in vivo role of MBL seems mainly to relate to the innate immune system as a humoral factor mediating some anti-microbial activity, which does not require maturation into self/non-self discrimination like the adaptive immune defence system based on T- and B-cell recognition (Janeway at al., 1999; Vorup-Jansen et al., 1998). The recognition of targets for MBL binding is mediated by the C-type lectin domain. C-type CRDs are found in proteins with a widespread occurrence, both in phylogenetic and functional perspective. In the case of MBL, the CRD recognizes preferentially hexcos with equatorial 3- and 4-OH groups, such as mannose and N-acetyl glucoseamin while carbohydrates which do not fulfill this sterical requirement, such as galactose and D-fucose, are not bound (Weis et al., 1992).

The terminal CRDs are distributed in such a way that to allow for binding of all three domains target surfaces should present binding sites with a spacing of approximately 53 Å (Sheriff et al., 1994; Weis & Drickamer, 1994). This property of 'pattern recognition' may contribute further to the selectively binding of microbial surfaces. The carbohydrate selectivity is obviously an important aspect of the self/non-self discrimination by MBL and is probably mediated by the difference in prevalence of mannose and N-acetyl glucoseamin residues on microbial surfaces, one example being the high content of mannose in the cell wall of yeasts such as *Saccharomyces cerevisiae* and *Candida albicans*. Carbohydrate structures in glycosylation of mammalian proteins are usually completed with sialic acid, which prevents binding of MBL to these oligomeric carbohydrates and thus prevents MBL recognition of self surfaces. Also, the trimeric structure of each MBL subunit may be of importance for target recognition.

Several studies have been carried out on aspects of the structure and biosynthesis of MBL by use of in vitro synthesis systems. The structure of the CRD of rat MBL-A was resolved by crystallizing recombinant protein produced in *E. coli* (Weis of al., 1992), and the structure of rat MBL-C has likewise been resolved by use of recombinant material (Ng et al., 1996). More recently, the crystal structure of the trimer of CRDs assembled through expressing both the 'neck-region' and the CRD have confirmed the earlier studies on the 'neck-region' as bringing together the three chains by hydrogen bonds between the colled-coil α-helices (Sheriff et at., 1994; Webs & Drickamer, 1994). The CRDs and 'neck-CRD' fragments of other collectins have likewise been expressed in *E. coli* based systems without the requirement of refolding protocols to gain functional activity. Thus, the in vitro synthesis of MBL domains can both with regard to the functional properties of carbohydrate recognition and the structural property of trimerisation efficiently be carried out in prokaryotic or simple eukaryotic expression systems.

In vitro synthesis of complete collectins by recombinant technique have mainly been attempted by use of mammalian c 11 lines, e.g., CHO and COS cells, as host cells. Attempts to express MBL in insect cells only resulted in low m.w. MBL (Ma et al., 1996), the recombinant proteins almost entirely consisting of subunits, dimers, and trimers of the MBL subunit chains.

Recombinant synthesis of human MBL in mammalian cell lines have been reported in several studies. In a study on opsonic function i.e., ability to enhance uptake by macrophages, of MBL, Kuhlman et al. (1989) used rMBL produced in CHO cells, which showed the same opsonic activity, as natural MBL. Characterization of the rMBL with regard to structure and post-translational modifications was not carried out. Likewise, Schweinle et al. (1993) produced rMBL and a truncated form of rMBL lacking the collagenous tail by stable transfection of CHO cells. Activity of the recombinant proteins was measured by C3 deposition on *Salmonella montevideo* preincubated with MBL and diluted human serum depleted of antibodies against *S. montevideo* as complement source. Surprisingly, the activity of recombinant full-length MBL was as high as for natural MBL though analysis of iodinated rMBL by ultracentrifugation showed the majority of the protein to be low molecular weight material. Comparison of the CHO cell produced rMBL with natural MBL concerning size, either through SDS-PAGE, ultracentrifugation or GPC, was not included. In a study by Super et al. (1992), GPC profiles of rMBL produced in mouse Sp2/OAg14 hybridoma cells were presented indicating that the size distribution of rMBL purified from the culture supernatant by carbohydrate affinity chromatography was markedly different from rMBL isolated through anti-MBL antibody affinity chromatography with respect to size distribution.

Recently, Ohtani et al. (1999) published data on human rMBL produced in CHO cells, which gave a yield of 120 $\mu$g per mL of culture medium. This was obtained using a expression vector allowing for selection of transfectants by G418 resistance and subsequent gene amplification through selection with methionine sulfoximine (MSX). Functional activity concerning carbohydrate selectivity was identical to the natural protein whereas some differences in the ability to activate complement was found as measured through lysis of erythrocytes. Both the GPC and SDS-PAGE analysis showed the presence of higher molecular weight forms of MBL though the total size distribution was noted by the authors to differ significantly from MBL purified from plasma. Interestingly, the hydroxylation pattern was essentially identical to natural MBL ven in the absence of added ascorbic acid. Concerning the post-translation modifications, it should be noted from this study that proper hydroxylation of rMBL does not warrant a structure similar to natural MBL.

The human MBL locus is polymorphic with three known mutations located in the protein encoding region (Sumiya et al., 1991; Lipscombe et al., 1992a; 1992b; Madsen et at., 1994) and others affecting regulatory elements of the gene (Madsen et al., 1995). All mutations apparently leads to a significantly lower level of MBL in body fluids from affected individuals. The spread in MBL concentration as measured in serum is thus about three orders of magnitude, ranging from 2–5 $\mu$g MBL/mL to less than 10 ng MBL/mL in individuals homozygous for the mutations affecting protein coding regions. The finding of MBL deficiency being associated with recurrent infections in children which were diagnosed as suffering from an opsonic defect (Super et al., 1989; Sumiya et al., 1991) emphasized the correlation between insufficient MBL levels and reduction in the defence against micro-organisms. In addition to the interaction with micro-organisms, collectins have also been suggested to mediate anti-viral defence (Hartshorn et al., 1993; Malhotra et at., 1994). In vitro studies on interaction with human immunodeficiency virus (HIV) showed MBL to inhibit infection of CD4 positive T and U937 cells. Clinical studies also suggest a role for MBL as a first-line defence against HIV. The period of time from the onset of symptoms of AIDS until the terminal stage seem to differ between MBL-deficient patients and patients with normal MBL levels. Also, the susceptibility to contract the infection appears to be significantly higher among MBL-deficient individuals as MBL deficiency occurs more frequently among HIV infected patients than healthy controls (Nielsen et al., 1995; Garred et al., 1997a). Hereditary complement deficiencies contribute to development of systemic lupus erythematosus (SLE) as have been shown for cases of C1, C2, and C4 deficiency (reviewed by Tan & Arnett, 1998). Several studies have suggested MBL deficiency likewise to be a risk factor in development of SLE (Davies et al., 1995; Lau et al., 1996; Ip et al., 1998) although the role of MBL is not well defined. One suggestion, following explanations for the other complement deficiencies as causative agents in SLE, argues that the defect in complement fixation due to MBL deficiency leads to poor immune complex clearance (Ip et al., 1998), thus pointing to MBL as a participant in maintaining homeostasis. Other clinical evidence suggests MBL to play an important role in reproductive biology. Recent reports show association between recurrent miscarriages and the MBL level (Kllpatrick et al., 1995; Christiansen et al., 1999).

A strategy for treating symptomatic MBL insufficient individuals aiming at reconstituting the MBL pathway has only been described in two studies. An opsonic detect observed among some children, at the time only characterized by the clinical manifestation of frequent infections, was treated by administering plasma (Soothill & Harvey 1976) while, in a more recent study, plasma-derived MBL was injected into a two-year-old girl (Valdimarsson et al., 1998). In both studies a health improvement was reported though the small number of patients involved in these studies obviously limits conclusions with regard to MBL as therapeutic agent. No clinical studies have been conducted with rMBL. A study by Ma et al. (1999) showed an antitumor activity of rMBL in mice mediated by a virus expression system.

As appears from the above, several attempts have been made to produce rMBL in in vitro systems in a form either identical to or with a high degree of resemblance to the natural protein. However, significant limitations have been demonstrated in the ability of the presently known in vitro synthesis systems to produce such rMBL.

SUMMARY OF THE INVENTION

In one aspect the present invention provides a novel form of MBL that is prepared by recombinant DNA technology in vitro or in vivo. More specifically, the invention concerns recombinant MBL (rMBL) in a novel form, which the inventors surprisingly found could be synthesized by the following process:

A process of producing a human recombinant mannan binding lectin (MBL) composition having a size distribution profile at least 50% identical to naturally occurring human MBL, comprising the steps of:
  preparing a gene expression construct encoding human MBL peptide or a functional equivalent thereof,
  transforming a host cell culture with the construct,
  cultivating the host cell culture, thereby obtaining expression and secretion of the polypeptide into the culture medium, followed by,
  subjecting said culture medium to affinity chromatography using a carbohydrate-derivatized matrix, said carbohydrate-derivatized matrix having at least a two-fold greater affinity for tetramers, pentamers, and/or hexamers of MBL subunit than for dimers of MBL subunits,
  obtaining an eluate comprising the human recombinant MBL composition.

By a functional equivalent to human MBL is meant a molecule having the function of human MBL, e.g., binding to microbial carbohydrates, mediating opsonising activity and/or activating complement as may be demonstrated by C4 deposition on a mannan-coated surface.

The functional activity of MBL may be estimated by its capacity to form an MBL/MASP complex leading to activation of the complement system. When C4 is cleaved by MBL/MASP an active thiol ester is exposed and C4 becomes covalently attached to nearby nucleophilic groups. A substantial part of the C4b will thus become attached to the coated plastic well and may be detected by anti-C4 antibody.

A quantitative TRIFMA for MBL functional activity was constructed by 1) coating microtitre wells with 1 mg mannan in 100 ml buffer; 2) blocking with Tween-20; 3) applying test samples, e.g. diluted MBL preparations 4) applying MBL deficient serum (this leads to the formation of the MBL/MASP complex); alternatively the MBL and the MBL deficient serum may be mixed before application with the microtitre wells; 5) applying purified complement factor C4 at 5 mg/ml; 6) incubate for one hour at 37° C.; 7) applying Eu-labelled anti-C4 antibody; 8) applying enhancement solution; and 9) reading the Eu by time resolved fluorometry. Between each step the plate is incubated at room temperature and washed, except between step 8 and 9.

Estimation by ELISA may be carried out similarly, e.g. by applying biotin-labelled anti-C4 in step 7; 8) apply alkaline phosphatase-labelled avidin; 9) apply substrate; and 10) read the color intensity. A calibration curve can be constructed using dilutions of one selected normal plasma. In relation to the present invention the following plasma is an example of useful plasmas: plasma pool LJ 6.57 28/04/97. The functionality may be expressed as the specific activity of MBL, such as in units of MBL activity per ng MBL.

Another assay for determining a functional equivalent to MBL is to determine the ability to bind to receptor/receptors on calls.

The interaction of MBL with receptor/receptors on cells may be analysed by cytofluorimetry. 1) MBL at a concentration of 50 $\mu$g/ml is incubated with $2\times10^5$ cells. The binding is carried out in phosphate buffered salt solution (PBS) containing 1% FCS and 0.1% Na-azide. 2) For detection of cell-bound MBL, biotinylated anti-MBL antibody is applied; 3) followed by the addition of strepavidin-FITC and 4) analysis of the mixture by fluorimetry.

A functional equivalent according to the invention fulfils at least one of the criteria discussed above, i.e. either activation of C4 or interaction with receptor(s) on cells, respectively. In a preferred embodiment both criteria are fulfilled.

By "recombinant human MBL" is meant human MBL which is expressed from engineered nucleic acids and by "MBL gene expression constructs" is meant an expression vector suitable for expression in the host cells.

By the term "composition having a size distribution profile at least 50% identical to naturally occurring human MBL" is meant that the size distribution of the various oligomers of MBL 50% identical on SDS-PAGE to human MBL purified from plasma by use of carbohydrate affinity chromatography. By 50% identical is meant that at least 50% of the oligomers has an apparent molecular weight higher than 200 kDa, when analysed by SDS-PAGE and/or Western blot, in determination of the amount of MBL having an apparent molecular weight higher than 200 kDa densitometic analysis may be used wherein protein bands on a SDS-PAGE gel is stained with protein-staining, e.g. silver staining or Coomassle Blue staining, or specific staining of Western blot using an MBL specific antibody.

By "purified recombinant MBL" is meant recombinant MBL purified from culture supernatants or body fluids or tissue from transgenic animals by use of carbohydrate affinity chromatography.

The present invention provides a form of MBL which is similar to natural human MBL, in that it in its purified form has a molecular size distribution profile closer to the natural human MBL than known up till now. Thus, in another aspect the invention relates to a recombinant human MBL composition comprising oligomers of MBL subunits, the size distribution profile of the oligomers being at least 50% identical to the size distribution of naturally occurring plasma human MBL.

In the present context the term "oligomer" refers to the various "mers" of MBL, such as monomer, dimer, trimer, tetramer, pentamer and hexamer. The monomer consists of three identical peptide chains, in the present context referred to as a subunit. The other oligomers are formed as combinations of 2–6 subunits.

As to expression of rMBL, the invention relates to a gene expression construct encoding a recombinant human mannan-binding lectin (MBL) polypeptide, comprising at least one intron sequence from the human MBL gene or a functional equivalent thereof, at least one exon sequence from the human MBL gene or a functional equivalent thereof, a promoter region different from the human MBL promoter, and an expression vector.

The expression is preferably carded out in e.g. mammalian cells, the preparation according to the invention results from the use of an expression vector comprising intron sequence(s) from an MBL gene and at least one exon sequence. Regarding the transgenic animals as expression system this term is in this context animals which have been genetically modified to contain and express the human MBL gene or fragments or mimics hereof.

By "recombinant MBL with structural properties under non-denaturing similar to natural human MBL" is meant recombinant MBL luting similarly from gel permeation chromatography analysis as human MBL as present in serum. By "recombinant MBL with structural properties under denaturing conditions similar to natural human MBL" is meant purified MBL with a size distribution on SDS-PAGE 50% identical to human MBL purified from plasma by use of carbohydrate affinity chromatography (as illustrated by FIG. 1). Thus, by "receombinant MOL" is meant MBL substantially free from any impurities naturally associated with MBL purified from plasma.

In this regard, mannose associated serine proteases (MASP's) are not regarded as impurities.

Accordingly, in another aspect the present invention relates to a process of producing a human recombinant mannan binding lectin (MBL), comprising the steps of:

preparing a gene expression construct as defined above encoding a human MBL polypeptide or a functional equivalent thereof, transforming a host cell culture with the construct, cultivating the host cell culture, thereby obtaining expression and secretion of the polypeptide into the culture medium, followed by, obtaining a culture medium comprising human recombinant MBL.

Also an aspect of the present invention is a process for isolating or purifying human MBL in order to obtain a composition of polypeptides having a size distribution which is at least 50% identical with naturally occurring human MBL.

Thus, the invention relates to a process of isolating a composition of human MBL oligomers having a size distribution at least 50% identical with naturally occurring plasma MBL comprising obtaining a preparation of human MBL oligomers, subjecting said preparation to affinity chromatography using a carbohydrate-derivatized matrix, said carbohydrate-derivatized matrix having a two-fold greater affinity for tetramers, pentamers, and/or hexamers of MBL subunit than for dimers of MBL subunit, and obtaining an eluate comprising the isolated human recombinant MBL composition.

In another aspect the invention concerns MBL, including rMBL, fragments or mimics hereof for use in the treatment of cancer and of conditions of diseases and disorders of eg the immune system and reproductive system, said treatment consisting of creation, reconstitution, enhancing and/or stimulating the opsonizing and bactericidal activity of the complement system, ie enhancing the ability of the immune defence to recognize and kill microbial pathogens. The application of rMBL similar to natural MBL in said treatment represents a great advantage over the application of known MBL, in particular plasma-derived human MBL, since the treatment with rMBL confers a much reduced risk of viral infection.

Said treatment may comprise cure and/or prophylaxis of diseases, disorders and/or conditions in need of treatment of cancer and of conditions of diseases and disorders of e.g. the immune system and reproductive system by humans and by animals having said functional units acting in this respect like those in humans. By condition in need of treatment is to be understood any condition in connection with current and/or expected need or in connection with an improvement of a normal condition. In particular, the treatment is a treatment of a condition of deficiency of MBL.

The invention further comprise pharmaceutical compositions containing MBL prepared according to the invention.

In yet an aspect the present invention concerns the use of MBL prepared according to the invention including fragments or mimics hereof, in the manufacture of a medicament or a pharmaceutical composition for the treatment comprising cure and/or prophylaxis of conditions of diseases and disorders of eg the immune system and reproductive system by humans and by animals having said functional units acting like those in humans.

Said diseases, disorders and/or conditions in need of treatment with the compounds of the invention comprise eg treatment of conditions of deficiency of MBL, treatment of cancer and of infections in connection with immunosuppressive chemotherapy including in particular those infections which are seen in connection with conditions during cancer treatment or in connection with implantation and/or transplantation of organs. The invention also comprises treatment of conditions in connection with recurrent miscarriage.

DETAILED DESCRIPTION OF THE INVENTION

The immune system has a considerable ability to prevent infections, which is of decisive importance for homeostasis and consequently survival and preservation of life. Therefore it is of considerable interest to identify compounds that are active in such processes. An intense research within this decade has uncovered Mannan-Binding Lectin (MBL) as a very versatile macromolecule, which eg is believed to be active in the innate immune system.

By the present invention it is possible to produce a human recombinant mannan binding lectin (MBL) composition having a size distribution profile at least 50% identical to naturally occurring human MBL as described above.

The MBL composition is produced as described above and subjected to an affinity chromatography capable of separating higher oligomers of MBL from the other oligomers.

The culture medium comprising a variety of MBL oligomers is subjected to an affinity chromatography on a carbohydrate-derivatized matrix.

Affinity chromatography is a well-known method for purifying proteins from a protein mixture. The carbohydrate-derivatized matrix has an least two-fold greater affinity for tetramers, pentamers and/or hexamers of MBL subunits than for dimers of MBL subunits. In a preferred embodiment the carbohydrate-derivatized matrix has an least three-fold greater affinity for tetramers, pentamer and/or hexamers of MBL subunits than for dimers of MBL. Also, the carbohydrate-derivatized matrix may have an least two-told greater affinity for tetramers, pentamers and/or hexamers of MBL subunits than for MBL subunits.

Thereby a MBL-composition having a size distribution being at least 50% identical, such as 60% identical, such as 70% identical, such as 80% identical, such as 90% identical, such as 95% identical, to naturally occurring MBL is provided. The size distribution is preferably substantially identical to naturally occurring MBL, whereby is meant that the identity is at least 99%.

The carbohydrate-derivatized matrix has substantially no affinity to subunits and/or dimers of MBL subunits. Preferably the carbohydrate-derivatized matrix has affinity for substantially only tetrameric, pertameric and/or hexameric recombinant MBL subunits.

It is preferred that the higher oligomers of the subunit, such as tetramers, pentamers and/or hexamers are dominating the composition. Thus, in the composition the ratio of tetramers, pentamers, and/or hexamers to subunits and/or dimers is preferably at least 2:1, preferably at least 5:1.

In a preferred embodiment, the ratio of the sum of tetramers, pentamers and hexamers to the sum of subunits and dimers is preferably at least 2:1, more preferably at least 5:1.

The matrix may be derivatized with any carbohydrate or carbohydrate mixture whereto MBL binds and for which binding of the higher oligomers of MBL are favored. The matrix is preferably a hexose-, such as a mannose- or a N-acetyl-glucosamin derivatized matrix, such as most preferably a mannose matrix.

The selectivity of the carbohydrate-derivatized matrix is obtained by securing that the matrix as such, i.e the un-derivatized matrix has substantially no affinity to MBL subunits, in particular no affinity to MBL trimers or smaller oligomers. This may be ensured when the matrix as such is carbohydrate-free in particular the matrix should not contain any Sepharose or the like. It is preferred that the matrix consists of a non-carbohydrate-containing polymer material, such as Fractogel®TSK beads.

The matrix may be in any form suitable for the chromatography, mostly in the form of beads, such as plastic beads.

After application of the culture media the column is washed, preferably by using non-denaturing buffers, having a composition, pH and ionic strength resulting in elimination of proteins, without eluting the highed oligomers of MBL. Such as buffer may be TBS. Elution of MBL is performed with a selective desorbing agent, capable of efficient elution of highed oligomers of MBL, such as TBS containing a desorbing agent, such as EDTA (5 mM for example) or mannose (50 mM for example), and MBL oligomers are collected.

According to the invention, the sequences from the MBL gene may be from the human MBL gone or from MBL genes of other animal species, in which the immune system in this respect is acting like the human immune system. An example of a preferred embodiment of a preparation of a recombinant MBL according to the invention is described in example 1 below, wherein said recombinant MBL is prepared by the use of an expression vector comprising sequences from the human MBL gene. An illustration of the expression vector in said preferred embodiment of the preparation method can be found in example 1 and in FIG. 2.

The invention also concerns the use of expression vectors comprising sequences, which are functional derivatives of the sequences of the human MBL gene. By said functional derivatives are meant sequences, which contain base pair alterations that lead to no functional or essentially no functional differences of the expression vector and the in this way prepared MBL has a functionality comparable to the MBL prepared by the use of an expression vector comprising the unaltered sequences from the human MBL gene.

In addition to the purification method it is preferred that the gene expression construct and the host call also favours production of higher oligomers.

Accordingly, the gene expression construct preferably comprises at least one intron sequence from the human MBL gene or a functional equivalent thereof.

Furthermore, the gene expression construct may comprise at least two exon sequences from the human MBL gene or a functional equivalent thereof. More preferably the gene expression construct comprises at least three exon sequences from the human MBL gene or a functional equivalent thereof. When comprising more than one exon, the exon sequences are preferably aligned as in the human MBL gone.

Although preferred that the sequence comprises intron sequences, it may for some applications be convenient that the expression construct comprises a cDNA sequence encoding a MBL subunit or a functional equivalent thereof.

The invention features the use of MBL gene expression constructs rather than MBL cDNA constructs for expression of rMBL in mammalian cell lines or transgenic animals to obtain recombinant MBL with structural properties under non-denaturing and denaturing conditions being substantially similar to natural human MBL. By "recombinant human MBL" is meant human MBL which is expressed from engineered nucleic acids and by "MBL gene expression constructs" is meant an expression vector suitable for expression in mammalian cell lines, which contains exon sequences and at least one intron sequence from the human MBL gene or from MBL genes of other animal species, such as but not limited to chimpanzees and rhesus monkeys.

Preferably, the DNA sequences encode a polypeptide sequence ac shown in SEQ ID NO: 1 or a functional equivalent, whereby a functional equivalent is as defined above. SEQ ID NO:1 corresponds to the MBL sequence having database accession NO: P 11226. The equivalent may be obtained by a modification of the peptide sequence shown as SEQ ID NO: 1, such as a sequence processing a corresponding property as the sequences mentioned in the present invention, but wherein one or more amino acids have been substituted with others. Preferably a functional equivalent contains conservative substitutions, i.e. where one or more amino acids are substituted by an amino acid having similar properties, such that a person skilled in the art of protein chemistry will expect the secondary and tertiary structure of the protein to be unchanged. Amino acids suitable for conservative substitutions include those having functionally similar side chains. For example, hydrophobic residues: e.g.

glycine, alanins, valine, leucine, isoleucine and methionine may replace another such residue. Similarly, conservative substitutions may involve interchanging hydrophilic residues:(e.g.: arginine and lysine, glutamine and aspargine, threonine and serine), basic reduces (e.g., lysine, arginine and histidine), and/or acidic residues (e.g., aspartic acid and glutamic acid). Functional equivalents may also, or alternatively, be modified by for example the deletion or addition of amino acids, or the chemical modification of amino acids, as long as the function of the polypeptide is preserved.

The isolated MBL peptide including any functional equivalents thereof, may in one embodiment comprise at least 80 amino acid residues, such as at least 100 amino acid residues, such as at least 150 amino acid residues, such as at least 200 amino acid residues, for example at least 220 amino acid residues, such as at least 250 amino acid residues.

In a preferred embodiment the expression vector is suitable for expression in mammalian cell lines or transgenic animals, which contains exon sequences and at least one intron sequence from the human MBL gene or from MBL genes of other animal species, such as, but not limited to, chimpanzes and rhesus monkeys. In one embodiment the host cell culture is cultured in a transgene animal. By a transgenic animal in this context is meant an animal which has been genetically modified to contain and express the human MBL gene or fragments or mimics hereof.

In a preferred embodiment the expression construct of the present invention comprises a viral based vector, such as a DNA viral based vector, a RNA viral based vector, or a chimeric viral based vector. Examples of DNA viruses are cytomegalo virus, Herpex Simplex, Epstein-Barr virus, Simian virus 40, Bovine papillomavirus, Adeno-associated virus, Adenovirus, Vaccinia virus, and Baculo virus.

In mammalian host cells, a number of viral-based expression systems may be utilized. In cases where an adenovirus is used as an expression vector, the nucleic acid molecule of the invention may be ligated to an adenovirus transcription/translation control complex, for example, the late promoter and tripartite leader sequence. This chimeric gene may then be inserted in the adenovirus genome by in vitro or in vivo recombination. Insertion in a non-essential region of the viral genome (for example, region E1 or E3) will result in a recombinant virus that is viable and capable of expressing a MASP-3 gene product in infected hosts (for example, see Logan and Sh nK, *Proc. Natl. Acad. Sci. USA* 81:3655–3659, 1984). Specific initiation signals may also be required for efficient translation of inserted nucleic acid molecules. These signals include the ATG initiation codon and adjacent sequences. In cases where an entire gene or cDNA, including its own initiation codon and adjacent sequences, is inserted into the appropriate expression vector, no additional translational control signal may be needed. However, in cases where only a portion of the coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153;516–544, 1987).

Examples of RNA virus are Semliki Forest virus, Sindbis virus, Poko virus, Rabies virus, Influenza virus, SV5, Respiratory Syncytial virus. Venezuela equine encephalitis virus, Kunjin virus, Sendai virus, Vesicular stomatitisvirus, and Retroviruses.

Examples of chimetic viruses are Adeno-virus, Sindbis virus and Adenovirus—adeno-associated virus.

Regarding specific vectors reference is made to Makrides, S. C., "Components of vectors for Gene Transfer and Expression in Mammalian Cells", which is hereby incorporated by reference.

In particular, an Epstein-Barr virus origin of replication or functional derivatives or mimics hereof including the pREP9 vector is used.

In one aspect the invention provides an expression construct encoding human MBL, featured by comprising one or more intron sequences from the human MBL gene including functional derivatives hereof. Additionally, it contains a promoter region selected from genes of virus or eukaryotes, including mammalla and insects.

The promoter region is preferably selected to be different from the human MBL promoter, and preferably in order to optimize the yield of MBL and size distribution of MBL oligomers, the promoter region is selected to function most optimally with the vector and host cells in question.

In a preferred embodiment the promoter region is selected from a group comprising Rous sarcoma virus long terminal repeat promoter, and cytromegalovirus immediate-early promoter, and elongation factor-1 alpha promoter.

In another embodiment the promoter region is selected from genes of microorganisms, such as other viruses, yeasts and bacteriae.

In order to obtain a greater yield of recombinant MBL, the promoter region may comprise enhancer elements, such as the QBI SP163 element of the 5' end untranslated region of the mouse vascular endothelian growth factor gene The construct is used for transforming a host cell to obtain a host call culture capable of expressing MBL.

The synthesis of the recombinant MBL may be by use of in vitro or in vivo cultures. The host cell culture is preferably an eucaryotic host call culture. By transformation of an eukaryotic cell culture is in this context meant introduction of recombinant DNA into the cells. The expression construct used in the process is characterized by having the MBL encoding region selected from mammalian genes including human genes and genes with big resemblance herewith such as the genes from the chimpanzee. The expression construct used is furthermore featured by the promoter region being selected from genes of virus or eukaryotes, including mammalian cells and calls from insects.

The present invention provides thus recombinant MBL, which is a form of MBL similar to natural human MBL, in that it in its purified form has a molecular size distribution profile closer to the natural human MBL than known up till now.

The process for producing recombinant MBL according to the invention is characterized in that the host cell culture is preferably eukaryotic, and for example a mammalian cell culture. A preferred host cell culture is a culture of human kidney cells and in an even more preferred form the host cells culture is a culture of human embryonal kidney cells (HEK cells). The invention features the use of HEK 293 cell lines for production of recombinant human MBL. By "HEK 293 cell lines" is meant any cell line derived from human embryonal kidney tissue such as, but not limited to, the cell lines deposited at the American Type Culture Collection with the numbers CRL-1573 and CRL-10852.

Other cells may be chick embryo fibroblast, hamster ovary cells, baby hamster kidney cells, human cervical carcinoma cells, human melanoma calls, human kidney cells, human umbilical vascular endothelium cells, human brain endothelium cells, human oral cavity tumor cells, monkey kidney cells, mouse fibroblast, mouse kidney cells, mouse connective tissue cells, mouse oligodendritic cells, mouse macrophage, mouse fibroblast, mouse neuroblastoma cells, mouse pre-B cell, mouse B lymphoma cells, mouse plasmacytoma cells, mouse teratocacinoma cells, rat astrocytoma cells, rat mammary epithelium cells, COS, CHO, BHK, 293, VERO, HeLa, MDCK, WI38, and NIH 3T3 cells.

In addition, a host cell strain may be chosen which modulates the expression of the inserted sequences, or modifies and processes the gene product in the specific fashion desired. Such modifications (for example, glycosylation) and processing (for example, cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. The mammalian cell types listed above are among those that could serve as suitable host cells.

In another aspect the present invention provides MBL that is prepared by recombinant DNA technology in e.g. mammalian cells or in transgenic animals. More specifically, the invention concerns recombinant MBL (rMBL), which is synthesized by preparing a gene expression construct as defined above encoding a human MBL polypeptide or a functional equivalent thereof, transforming a host cell culture with the construct, cultivating the host cell culture, thereby obtaining expression and secretion of the polypeptide into the culture medium, followed by, obtaining a culture medium comprising human recombinant MBL.

Furthermore, the invention relates to the synthesis of MBL by (a) preparation of an expression construct encoding human MBL;

(b) transformation of a eukaryotic cell culture with said expression construct and thereby obtain an eukaryotic recombinant host cell culture;

(c) growth of said recombinant host cell culture either in vitro or in form of a transgenic animal and thereby express said human MBL;

(d) harvest of said expressed human MBL and purification hereof by means of affinity chromatography as described above.

The most cell culture may be cultured in any suitable culture medium. Example of culture medium are RPMI-1640 or DMEM supplemented with, e.g., insulin, transferrin, selenium, and foetal bovine serum.

The invention further consists of a step for purification or isolation of human MBL, such as human MBL from culture supernatants or from body fluids or tissue from transgenic animals by use of carbohydrate affinity chromatography as described above. In a preferred embodiment of the invention the affinity chromatography is performed by means of matrices of mannose, hexose or N-acetyl-glucoseamin derivatized matrices, which are suitable for affinity chromatography as described above. In particular, an affinity chromatography is used, in which the matrices have been derivatizised with mannose. Previously the use of matric s derivatizised with mannan has been employed to harvest recombinant MBL from culture supernatant. While mannan-derivatized matrices binds both high and low molecular weight forms of MBL, the use of matrices derivatizised as described above such as with mannose offers an surprising advantage in the purification of recombinant MBL as this matrix selectively bind the form of recombinant MBL that resemble natural MBL. The degree of similarity to the natural MBL is measured to be more than 50% in analysis of the size distribution by SDS-PAGE followed by protein staining of the gel as known in the prior art, see e.g. Ma et al. (1997).

Purified recombinant MBL is in this context to be understood as recombinant MBL purified from cell culture supernatants or body fluids or tissue from transgenic animals purified by use of carbohydrate affinity chomatography.

The process of isolating or purifying a composition of human MBL oligomers having a size distribution at least 50% identical with naturally occurring plasma MBL preferably comprises obtaining a preparation of human MBL oligomers, subjecting said preparation to affinity chromatography using a carbohydrate-derivatized matrix, said carbohydrate-derivatized matrix having a two-told greater affinity for tetramers, pentamers and/or hexamers of MBL than for dimers of MBL, and obtaining an eluate comprising the isolated human recombinant MBL composition.

The present invention provides a novel form of recombinant MBL composition comprising oligomers of MBL subunits, the size distribution profile of the oligomers being at least 50% identical to the size distribution of naturally occurring plasma human MBL in a preferred embodiment the size distribution is at least 60% identical, such as 70% identical, such as 80% identical, such as 90% identical, such as 95% identical, to naturally occurring MBL is provided.

It is preferred that the higher oligomers of the subunit, such as tetramers, pentamers and/or hexamers are dominating the composition. Thus, in the composition the ratio of tetramers, pentamers, and/or hexamers to subunits and/or dimers is preferably at least 2:1, preferably at least 5:1.

In a preferred embodiment, the ratio of the sum of tetramers, pentamers and hexamers to the sum of subunits and dimers is preferably at least 2:1, more preferably at least 5:1.

When estimating the size distribution of the oligomers of the MBL composition the size distribution is assessed by Western blotting on a SDS-PAGE. Hereby it may be seen that 50% means that more than 50% of the rMBL has an apparent molecular weight higher than 200 kDa when analysed by SDS-PAGE and/or Western blot.

The recombinant MBL composition may be purified by any suitable means from the culture medium, such as by any physicochemical isolating method, including but not limited to filtration methods, chromatography, such as ion-exchange chromatography based on size, gel permeation chromatography or affinity chromatography. The recombinant MBL composition is preferably purified from the culture medium by means of affinity chromatography as discussed above.

The functionality of the recombinant MBL composition is preferably resembling the functionality of plasma or serum MBL. In the present context the functionality of MBL is meaning the capability of activating the complement system as discussed above in relation to functional equivalents. The functionality may be expressed as the specific activity of MBL, such an units of MBL activity per ng MBL. The functionality the recombinant MBL composition as expressed as specific activity is preferably at least 25% of the specific activity of MBL purified from serum, such as at least 50% of the specific activity of MBL purified from serum, more preferred at least 75% of the specific activity of MBL purified from serum.

The MBL composition according to the invention is substantially free from any impurities naturally associated with the MBL when produced in a native host organism, such as from any impurities naturally associated with the MBL purified from serum By a native host organism is meant that MBL is produced by a cell normally expressing MBL.

The eluant obtained from the affinity chromatography may be used as such for preparing a pharmaceutical composition, or the eluant may be subjected to further purification steps before being used.

The MBL composition obtained by the present invention may be used for the preparation of a pharmaceutical composition for the prevention and/or treatment of various diseases or conditions.

In addition to the MBL oligomers, the pharmaceutical composition may comprise a pharmaceutically acceptable carrier substance and/or vehicles.

In particular, a stabilising agent may be added to stabilize the MBL proteins. The stabilising agent may be a sugar alcohol, saccharide, protein and/or amino-acids. An example of a stabilising agent may be albumin or maltose.

Other conventional additives may be added to the pharmaceutical composition depending on administration form for example.

In one embodiment the pharmaceutical composition is in a form suitable for injections. Conventional carrier substances, such as isotonic saline, may be used.

In another embodiment the pharmaceutical composition is in a form suitable for pulmonal administration, such as in the form of a powder for inhalation or creme or fluid for topical application.

The present invention is based upon the synthesis of a novel form of recombinant MBL, which form is closer to the natural human MBL than achieved up till now and which can be synthesized by use of in vitro or in vivo technology. Based upon the evidence for the important role of MBL in the immune defence, this provided form of recombinant MBL offer the surprising possibility of treatment of conditions such as cancer and of infections in connection with immunosuppressive chemotherapy. The structural differences between the previously reported preparations of recombinant MBL compared to the natural form of MBL made any such treatment unlikely. Also, the application of rMBL similar to natural MBL in said treatment represents a great advantage over the application of known MBL, in particular plasma-derived human MBL, since the treatment with rMBL confers a much reduced risk of viral infection.

The treatment needs not be a treatment of a diagnosed disease, disorder or condition in a presently or apparently need of treatment but may be used to prevent the disease or condition to occur.

A treatment in this context may comprise cure and/or prophylaxis of e.g. the immune system and reproductive system by humans and by animals having said functional units acting in this respect like those in humans. By conditions to be treated are not necessarily meant conditions presently known to be in a need of treatment, but comprise generally any condition in connection with current and/or expected need or in connection with an improvement of a normal condition. In particular, the treatment is a treatment of a condition of deficiency of MBL.

In another aspect of the present invention the manufacture is provided of a medicament consisting of said pharmaceutical composition of MBL, including compositions of rMBL fragments or mimics hereof intended for treatment of conditions comprising cure and/or prophylaxis of conditions of diseases and disorders of e.g. the immune system and reproductive system by humans and by animals having said functional units acting like those in humans.

Said diseases, disorders and/or conditions in need of treatment with the compounds of the invention comprise eg treatment of conditions of deficiency of MBL, treatment of cancer and of infections in connection with immunosuppressive chemotherapy including in particular those infections which are seen in connection with conditions during cancer treatment or in connection with implantation and/or transplantation of organs. The invention also comprises treatment of conditions in connection with recurrent miscarriage.

Thus, in particular the pharmaceutical composition may be used for the treatment and/or prevention of clinical conditions selected from infections, MBL deficiency, cancer, disorders associated with chemotherapy, such as infections, diseases associated with human immunodeficiency virus (HIV), diseases related with congenital or acquired immunodeficiency. More particularly, chronic inflammatory demyelinating polyneuropathy (CIDP, Multifocal motorio neuropathy, Multiple scelrosis, Myasthenia Gravis, Eator-Lambert's syndrome, Opticus Neuritis, Epilepsy; Primary antiphosholipid syndrome; Rheumatoid arthritis, Systemic Lupus erythematosus, Systemic scleroderma, Vasculitis, Wegner's granulomatosis, Sjegren's syndrome, Juvenile rheumatoid arthritis: Autoimmune neutropenia, Autoimmune haemolytic anaemia, Neutropenia; Crohn's disease, Colitis ulcerous, Coellac disease: Asthma, Septic shock syndrome, Chronic fatigue syndrome, Psoriasis, Toxic shock syndrome, Diabetes, Sinusitis, Dilated cardiomyopathy, Endocarditis, Atherosclerosis, Primary hypo/agammaglobulinaemia including common variable immunodeficiency, Wiskot-Aldrich syndrome and serve combined immunodefiency (SCID), Secondary hypo/agammaglobulinaemia in patients with chronic lymphatic leukaemia (CLL) and multiple myeloma, Acute and chronic idiopathic thrombocytopenic purpura (ITP), Allogenic bone marrow transplantation (BTM), Kawasaki's disease, and Guillan-Barre'syndrome.

The route of administration may be any suitable route, such es intravenously intra musculary, subcutanously or intradermally. Also, pulmonal or topical administration is envisaged by the present invention.

In particular the MBL composition may be administered to prevent and/or treat infections in patients having clinical symptoms associated With congenital or acquired MBL deficiency or being at risk of developing such symptoms. A wide variety of conditions may lead to increased susceptibility to infections in MBL-deficient individuals, such as chemotherapy or other therapeutic cell toxic treatments, cancer, AIDS, genetic disposition, chronic infections, and neutropenla.

It appears that cancer patients treated by chemotherapy are often susceptible to infection due to adverse effects of the drug regime on cells of the immune system, which is the background for the use of MBL therapy in the treatment of this condition. The observed low plasma concentrations of MBL (below 500 ng/mL) are indicative for an increased susceptibility to clinical significant infections and the immune defence of these patients can be reinforced by administration of recombinant or natural plasma-derived MBL.

The pharmaceutical composition may thus be administered for a period before the onset of administration of chemotherapy or the like and during at least a part of the chemotherapy.

The MBL composition may be administered as a general "booster" before chemotherapy, or it may be administered to those only being at risk of developing MBL deficiency. The group of patients being at risk may be determined be measuring the MBL level before treatment and only subjecting those to treatment whose MBL level is below a predetermined level. The limit for determining a low MBL level is evaluated to be below 500 ng/ml for most groups. The MBL level may be determined by time resolved immunofluorescent assay as described in Example 9, ELISA, RIA or nephelometry.

Another indication for administering MBL is when the MBL level is below 50% of the normal level, such as below 300 ng/ml, or below 200 ng/ml.

The MBL composition is administered in suitable dosage regimes, in particularly it is usually administered at suitable intervals, eg. once or twice a week during chemotherapy.

Normally from 1–100 mg is administered per dosage, such as from 2–10 mg, mostly from 5–10 mg per dosage. Mostly about 0.1 mg/kg body weight is administered.

Thus, in one aspect the invention concerns MBL, including rMBL, fragments or mimics hereof for use in the treatment of cancer and of conditions of diseases and disorders of e.g. the immune system and reproductive system, said treatment consisting of creation, reconstitution, enhancing and/or stimulating the opsonic and/or bactericidal activity of the complement system, i.e. enhancing the ability of the immune defence to recognize and kill microbial pathogens.

Furthermore, an aspect of the present invention is the use of a recombinant composition according to the present invention in a kit-of-parts further comprising another medicament. In particular the other medicament may be an anti-microbial medicament, such as antibiotics.

Concerning miscarriage, it has been reported that the frequency of low plasma levels of MBL is increased in patients with otherwise not explained recurrent miscarriages, which is the background for lowering of the susceptibility to miscarriage by a reconstitution of the MBL level by administration of recombinant MBL in these cases.

As to the nature of compounds of the invention, it appears, that in its broad aspect, the present invention relates to compounds which are able to act as opsonins, that is, able to enhance uptake by macrophages either through direct interaction between the compound and the macrophage or through mediating complement deposition on the target surface. A particular example hereof is MBL, a fragment or a mimic hereof. The present invention is based upon the disclosure of a synthesis of a recombinant human MBL which appears to be closer to the structure of the natural human MBL than achieved in the past.

The invention has now been explained and accounted for in various aspects and in adequate details, but additionally it will be illustrated below by FIGS. 1 and 2 and the non-limiting examples of preferred embodiments.

EXAMPLES

Example 1

Figure 1:
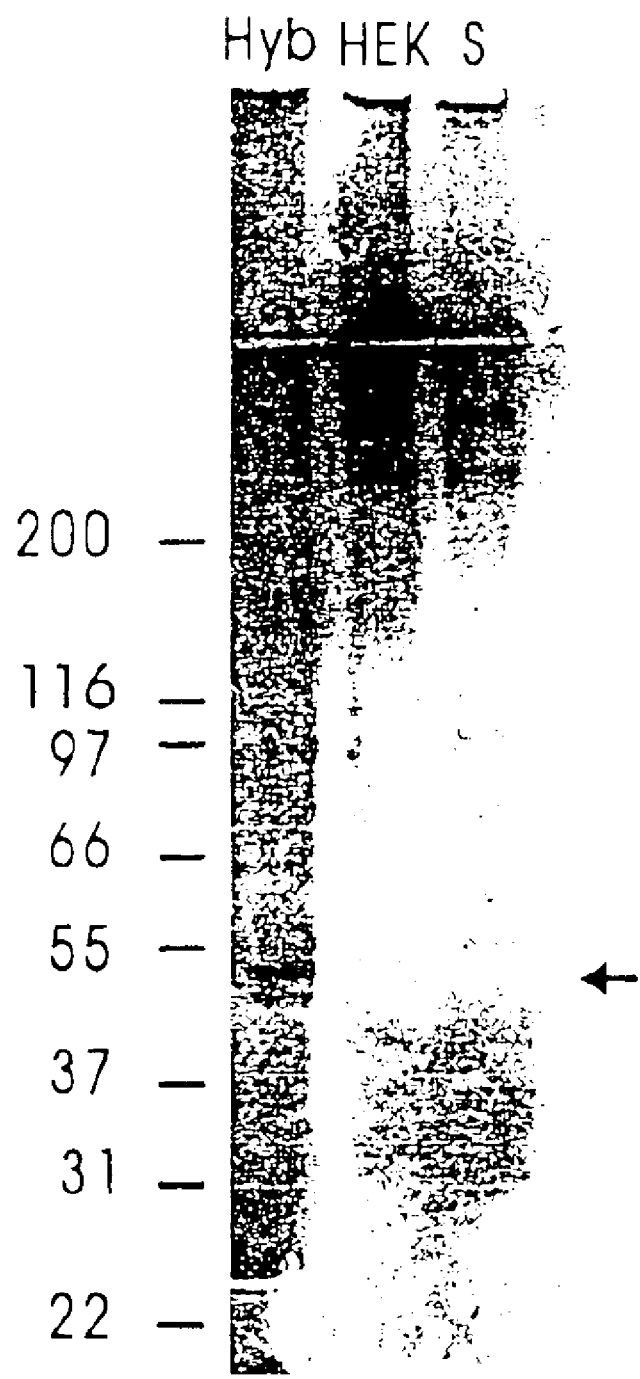
FIG. 1 shows purified recombinant and native MBL compared analysed in the non-reduced state by SDS-PAGE and silver staining (stacking gel included). Lane 'S' was loaded with 24 ng of natural MBL (MO-04, The State Serum Institute), Lane "HEK" with 60 ng of rMBL produced in HEK 293EBNA cells and Lane 'Hyb' with 12 ng of rMBL produced in Sp2/0Ag14 cells (supplied by Dr. R. A. B. Ezekowitz). Arrow shows the position of the predominant form in the hybridoma cell-produced rMBL. Although the amount rMBL In Lane 'HEK' is 5 times higher than In Lane 'Hyb', no band 55 kDa band can be seen in Lane 'HEK', suggesting a significant difference in the disulfide bridge formation of the two rMBL subunits. (As discussed in Example 6

Human genomic DNA was isolated from 20 mL of blood drawn into EDTA. The EDTA/blood was mixed with 80 mL of cold (4° C.) 10 mM Tris-HCI, 5 mM $MgCl_2$, 1% (v/v) Triton X-100, 0.32 mM sucrose, and left to incubate at 4° C. for 30 min with occasional agitation. The sample was centrifuged at 1000×g for 30 min at 4° C., followed by discharge of the supernatant and a brief rinse of the nuclei-containing pellet in approximately 10 mL of 0.9% (w/v) of NaCl. The collected nuclei were resuspended in 6 mL of 75 mM NaCl, 24 mM EDTA [pH 8.01], and 460 µL of 10% (w/v) SDS and 1 mg pronase (cat. no. 165921, Boehringer-Mannheim, Mannheim, Germany) was added. After o/n incubation at RT with gentle agitation, 2 mL of a saturated (~6 M) NaCl solution was added. Following vigorous agitation, the debris was removed by centrifugation at 1000× g. Isopropanol was added 1:1 to the supernatant and the vial was gently shaken until the DNA precipitate appeared. The thread-like precipitate was collected on a sealed Pasteur pipette, washed on the sealed tip in 70% (v/v) ethanol, air-dried and finally resuspended in 1 mL of TE-buffer. PCR amplification of the MBL gene was carried out with a sense-primer modified to contain an Xhol site: 5'-AGATTAACCTTCCtcGAGTTTTCTCACACC-3' (SEQ ID NO:2). The anti-sense primer was modified to contain a BamH1 site: 5'-TAACggaTCCACTCCAATAATACATACAC-3' (SEQ ID NO:3) (restriction sites engineered into the sequences are underlined and modified basepairs compared to the natural gene sequence as published by Sastry et al. (1989) are show as lower case letters in both primer sequences. Primers were produced by DNA technology, Aarhus, Denmark). The sense and anti-sense primers were located in the 5' and 3' UTRs respectively. Reaction conditions for the PCR consisted of 200 μM dATP, 200 μM dCTP, 200 μM dGTP, 200 μM dTTP (cat. no. 1969064, Boehringer-Mannheim), reaction buffer at 1 × strength, 0.75 μL of enzyme (cat. no. 1732641, Expand High Fidelity™, Boehringer Mannheim, reaction buffer supplied with enzyme), genomic DNA (100 ng), and water to a final volume of 50 μL. The PCR thermal program performed 1 cycle at 96° C. for 3 min, 10 cycles of 94° C. for 15 s, 60° C. for 30 s, and 72° C. for 5 min, followed by 20 cycle of 94° C. for 15 s, 60° C. for 30 s, and 68° C. for 5 min with a time increment of 20 s per cycle, followed by a final elongation step at 72° C. for 5 min (Omn 15 E™ thermal cycler, Hybaid, Ashford, UK). Cloning of the 6.2 kb PCR product into the pCR2 vector by use of the TA cloning kits™ (cat. no. K2000-01, Invitrogen, Leek, The Netherlands) was carried out according to the manufactures' recommendations. The MBL gene was isolated from the pCR2 by digesting the vector with NoId and BamHI enzymes (cat nos. 15441-025 & 15201-023, GibcoBRL, Paisley, UK) for 6 h at 37° C. in an appropriate buffer. The insert DNA, i.e., the 5'-Not I-MBL-BamHl-3' fragment, was isolated from an 1% (w/v) agarose gel by use of Pharmacia's Bandprep™ kit (cat. no. 27-9285-01, Pharmacia, Uppsala, Sweden). The pREP9 vector (cat. no. V009-50, Invitrogen) was digested as described for the MBL/pCR2 vector and the restriction product, i.e., the linearized vector, was likewise isolated from agarose to minimize contamination with undigested vector. In a final volume of 10 μL, 1 μL (~100 ng) of digested pREP9 vector, 4 μL (~400 ng) of 5'-NotI-MBL-BamHI-3', ligation buffer at 1× strength and 20 units of T4 ligase (cat. no. 202S, New England Biolabs, Beverly, Mass., reaction buffer supplied with enzyme) was incubated o/n at 14° C. *E. coli* TOPF10 cells were made transformation competent by $CaCl_2$ permeabilising and transformed with the ligation product by heat-shock as described by Hanahan (1983). The bacteria were spread onto LB-agar plates supplemented with 50 μg ampicilin/mL, and colonies appeared after o/n incubation at 37° C.

Figure 2:
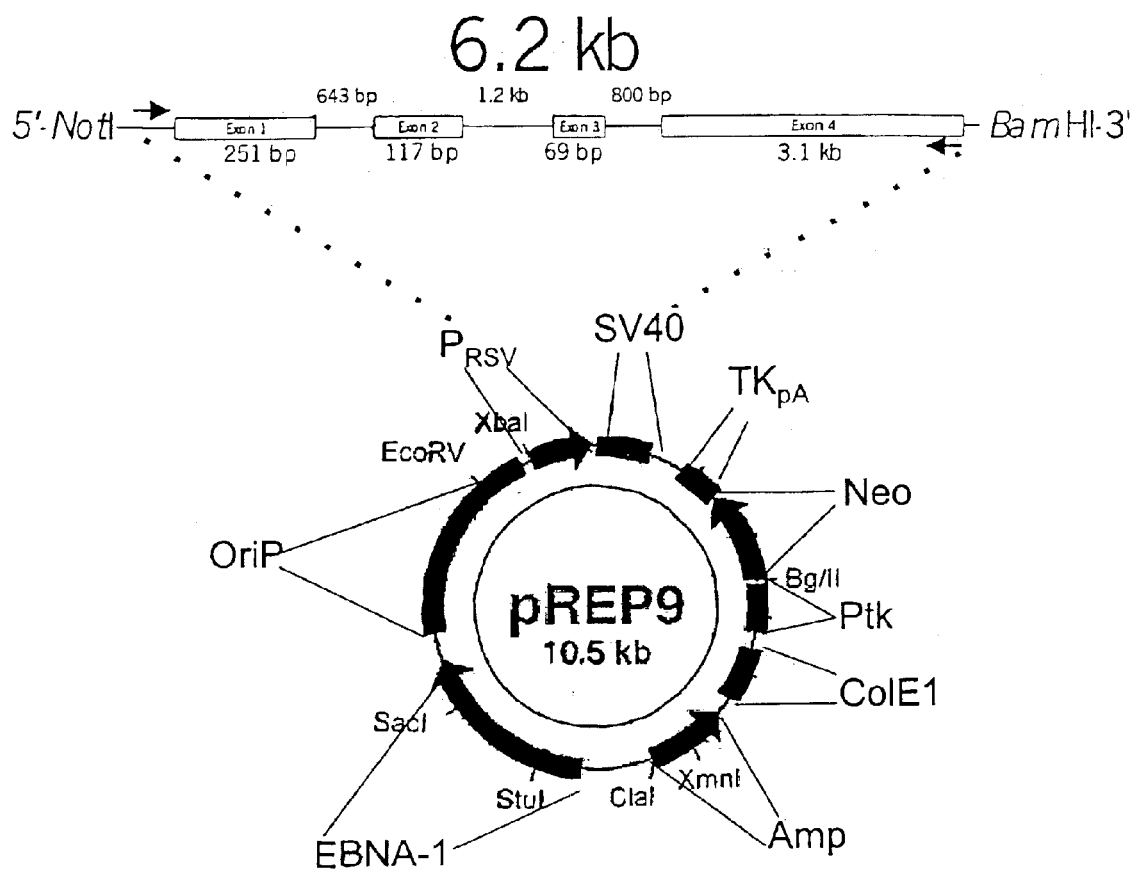
FIG. 2 shows a sketch of a preferred expression construct according to the invention viz. the MBL/pREP9 construct as discussed in Example 1.
Figure 3:
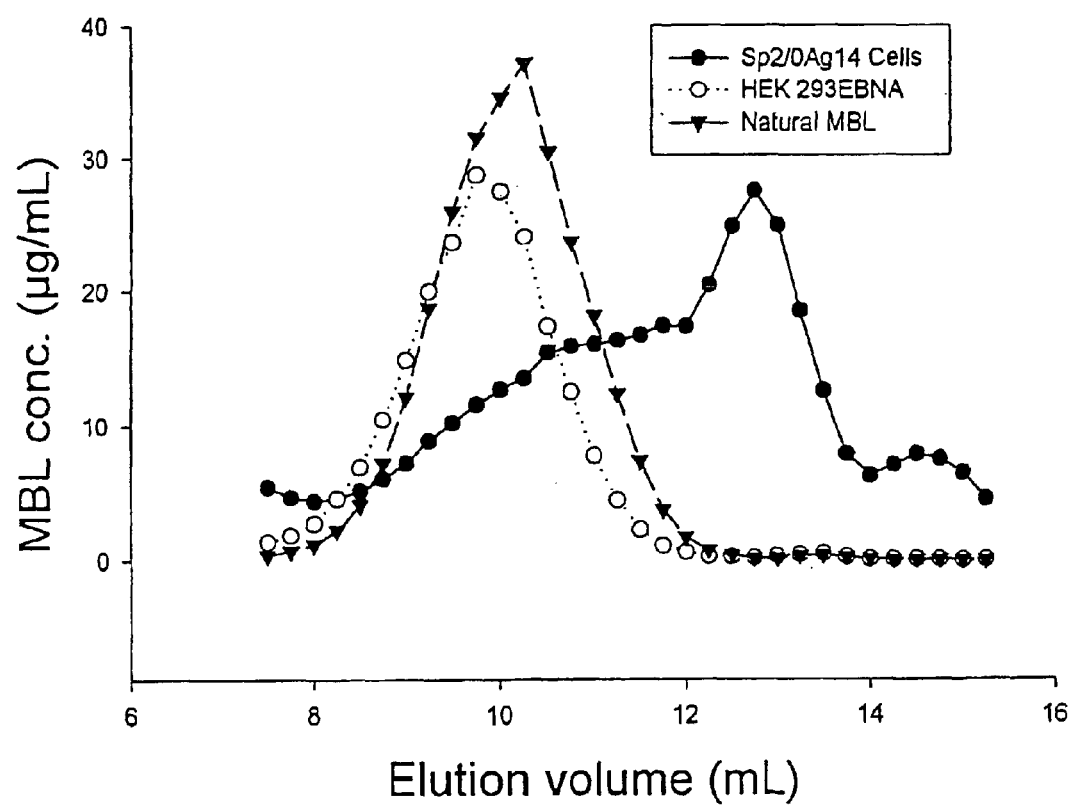
FIG. 3 shows MBL concentrations in fractions (stated as elution volume) from gel permeation chromatography analysis (Example 7).

FIG. 2 shows a sketch of a preferred expressions construct according to the invention viz. the MBL/pREP9 construct. The PCR amplified (the location of sense and antisense primers are indicated black with arrows) part of the MOL gene contained the four exons, including the entire known 3' untranslated of exon 4 as determined by Sastry et al. 1989. The fragment was merged with the expression vector, named pREP9, in the NotI and Bam HI endonuclease restriction sites (the EcoRV, XbaI, BglII, XmnI, ClaI, StuI and SacI restriction endonuclease sites in the vector sequence are also indicated). Transcription of the MBL fragment cloned into the pREP9 expression vector was controlled by the Rous sarcoma virus long terminal repeat promoter ($P_{RSV}$) located upstream to the cloning site (direction of the transcription for elements of the vector are indicated with arrow heads) and with a simian virus 40 (SV40) polyadenylation site. Bacterial propagation, that is, production of vector DNA in *E, coli*, was obtained through an ampicilin resistance marker (Amp) and a ColE1 prokaryot 'origin of replication'. Maintenance of the vector in HEK293EBNA cells was conferred by the Epstein-Barr virus origin of replication (OriP) and expression of the Epstein-Barr virus nuclear antigen 1 (EBNA-1), which attaches the vector to the host cell chromosomes.

Example 2
Expression of Recombinant MBL in Mammalian Cells:
HEK 293EBNA cells, grown until confluence in 150 cm² flasks (cat.no. 9075, TPP AG) containing DMEM (Biological industries) supplemented with 10% FBS, glutamin, 200 μg G418/mL (Geneticin™, cat.no. G9516, Sigma) and antibiotics (10,000 units penicillin and 0.1% (w/v) streptomycin), were harvested by trypsination and seeded in a four fold lower density (~25% confluence) into 150 cm² flasks (cat.no. 90150, TPP) 24 h prior to transfection. Three hours prior to transfection all medium was renewed. In a total volume of 1680 μL, 60 μg of the MBL/pREP plasmid DNA (reference is made to Example 1) was mixed with 150 mM NaCl, 1 mM EDTA, 10 mM Tris-HCl (pH 7.12), 268 mM $CaCl_2$. The DNA, calcium solution was added into 1680 μL of 50 mM HEPES, 250 mM NaCl, 1.5 mM $Na_2HPO_4+NaH_2PO_4$ adjusted to pH 7.12. The cells were incubated for 14–15 h with the DNA/Ca-$PO_4$ precipitate, rinsed twice in PBS and further incubated with RPMI-1640 medium (50 mL per bottle) supplemented with glutamin, antibiotics (penicillin and streptomycin) and insulin-transferrin-selenium (ITS) solution (cat.no. 51300-44, GibcoBRL) for 6–8 d.

Example 3
Purification of rMBL by Use of Carbohydrate-Derivatizised Matrices.

Figure 4:
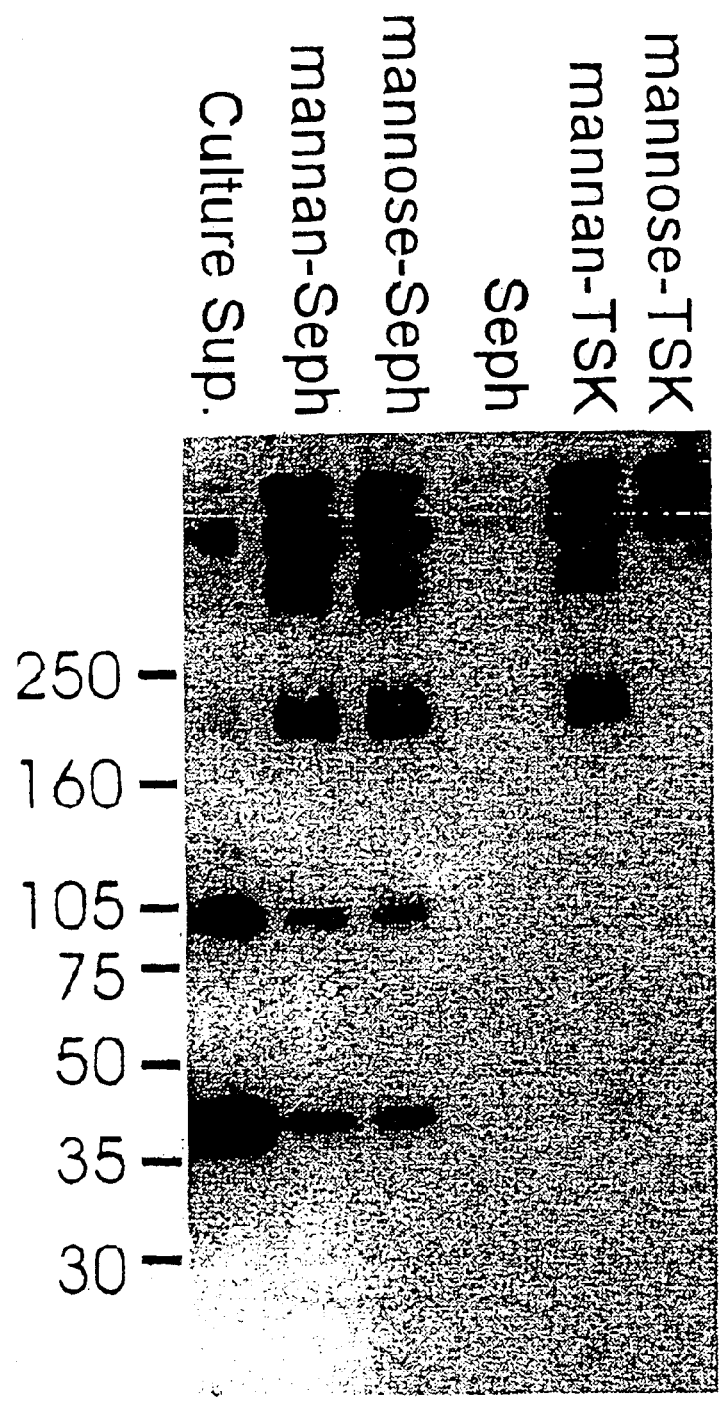
FIG. 4 shows a Western blot analysis of rMBL purified by mannose-TSK beads, mannan-TSK beads, mannose-Sepharose beads, mannan-Sepharose beads and underivatizised Sepharose 48 beads. For comparison unfractionated culture supernatant from MBL/pREP9 transfected cells was included (Example 3).
Figure 5:
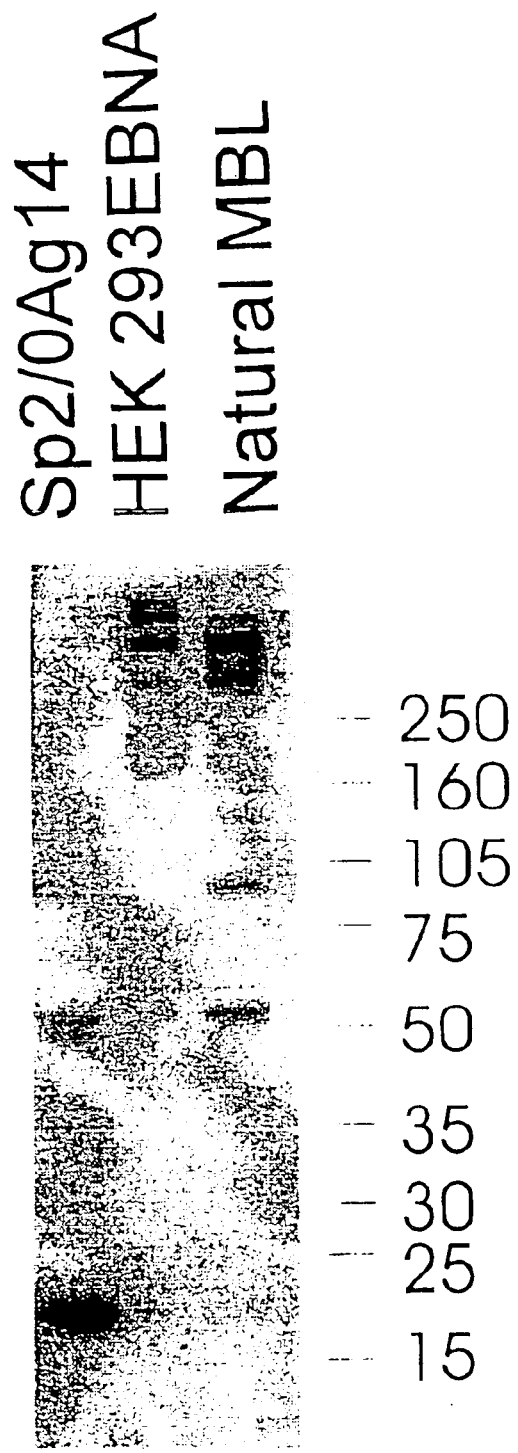
FIG. 5 shows a Western blot of two preprations of rMBL analysed in the non-reduced state: 50 ng rMBL produced according to the present invention ('293 EBNA cells') and 50 ng rMBL preparations produced according to the method described by Super et al., 1992 (Sp2/0Ag14 cells. Natural MBL purified from human serum as described by Lu et al. 1990 ('Natural MBL') (Example 6).

Fractogel TSK HW-75 beads (cat.no. 14985, Merck KgaA, Darrnstadt, Germany) were activated by mixing 50 mL of beads with 50 mL of 0.5 M $Na_2CO_3$ (pH 11) and 10 mL of vinyl sulfone (cat.no. V370-0, Aldrich, Milwaukee, Wis.), followed by incubation with agitation for 1½ h at RT. The beads were collected on a glass filter and washed once in $H_2O$ and once in 0.5 M $Na_2CO_3$ (pH 11). Beads were resuspended in 0.5 M $Na_2CO_3$ (pH 11) and mannose added to a final concentration of 10% (w/v). The mixture was left to incubate with agitation o/n at RT. Following rinse in $H_2O$, residual reactive groups were blocked by incubating the beads in 0.1 M ethanolamine (pH 9) for 2 h. After a rinse in $H_2O$ and TBS, 5 mL of mannose-coupled TSK-75 was packed on a chromatography column and washed in 15 mL of 0.1 M glycin (pH 3.0) and equilibrated in TBS/0.05% (v/v) Tween-20.2 mM $CaCl_2$ until UV-absorption remained stable. Culture medium from MBL/pREP9 transfected cells, cleared by centrifugation at 5000×g, was passed over the column at 0.4 mL/min. The column was washed in 76 mL of TBS, 2 mM $CaCl_2$, and the bound rMBL eluted in TBS, 5 mM EDTA and collected in fractions of 500 μL. To prepare TSK beads with mannan (purified from yeast as described by Nakajima & Ballou, 1974), the beads were activated as described above and incubated with 25 mg mannan/mL 0.5 M $Na_2CO_3$ (pH 11) followed by the same treatment as for preparation of mannose-derivatized beads. Sepharose 4B (cat.no. 17-0120-01, Pharmacia, Uppsala, Sweden) beads were derivatized with mannose and mannan as described for the TSK beads. Eluates from the three matrices were analyzed Western blotting as described in Example A, loading 7 ng of rMBL purified by mannose-TSK beads, mannan-TSK beads, mannose-Sepharose beads, and mannan-Sepharose beads into separate lanes of the SDS-PAGE gel. For comparison unfractionated culture supernatant corresponding to 7 ng of rMBL was loaded in a lane. The Western blot is shown in FIG. 4.

Example 4
Analysis of MBL Under Non-Denaturing Conditions by Gel Permeation Chromatography Permeation chromatography of purified rMBL or culture medium containing rMBL was performed on a Superose-6 column (Superose 6™ HR 10/30, cat.no. 17-0537-01, Pharmacia) equilibrated in 5 mM EDTA, TBS,0.01% (v/v) Tween-20 [pH 7.4]. A sample volume of 100 μL was passed over the column with a flow rate of 0.5 mL/min. Fractions were collected 5 mL post sample injection in volumes of 250 µL.

Example 5
Analysis of MBL Under Denaturing Conditions by SDS-PAGE/Silver-Staining SDS-PAGE 4%–20% gradient gels were prepared and used in electrophoresis as described by Jensen et al. (1997). The procedure for silver staining was adopted from Nesterenko et al. (1994). The PAGE gels were fixed in 100 mL 50% (v/v) acetone, 6.25 mL tricholoroacetic acid, 0.85% (v/v) formaldehyde for 15 min, followed by rinsing trice in $H_2O$, and washing for 15 min in $H_2O$. The gel was incubated in 100 mL of 50% (v/v) acetone for 15 min followed by incubation for 1 min in 0.67 mM $Na_2S_2O_3$, and three rinses in $H_2O$. Impregnation of the gel with silver nitrate was carried out in 15 mM $AgNO_3$, 0.9% (v/v) formaldehyde, followed by rinsing three times in $H_2O$. The gel was developed by incubating in 0.19 mM $Na_2CO_3$, 0.9% (v/v) formaldehyde, 0.67 mM $Na_2S_2O_3$ for approx. 3 min. The precipitation was stopped by incubation of the gel for 3 min in 1% (v/v) acetic acid and preserved in 25% (v/v) ethanol, 3% (v/v) glycerol.

Example 6
Analysis of rMBL by SDS-PAGE Followed by Western Blotting

Tris buffered saline (TBS) and phosphate buffered saline (PBS), all adjusted to pH 7.4 were prepared as described by Sambrook et al. (1989). For blocking non-specific protein interactions, the buffers were supplemented with 0.05% (v/v) Tween-20 (TBS/Tw and PBS/Tw). SDS-PAGE 4%–20% gradient gels were prepared and used in electrophoresis as described by Jensen et al. (1997). 50 ng of rMBL produced in HEK 293EBNA cells (prepared according to the present invention), 50 ng of rMBL prepared as described by Super et al. (1992), and 50 ng of MBL prepared from human plasma (MO012, State Serum institute) was loaded onto the gel in the non-reduced state. Proteins were transferred onto Amersham's Hybond™-P membrane (cat.no. RPN303F) by semi-dry blotting in 50 mM Tris-base, 40 mM glycin, 3.7% (w/v) SDS, 20% (v/v) ethanol for 60 Vxh. Non-specific protein interactions were blocked by incubating the membrane with 0.1% Tween-20 for ½ h, For detection of MBL, the membrane was incubated with a monoclonal antibody raised against human MBL (Hyb 131-1, State Serum Institute) diluted to 1 µg ml in TBS, 0.05% Tween-20. 1 mM EDTA, 1 mg HSA/mL (cat.no. 44 05 11, State Serum institute), 1 mg human IgG/mL (cat.no. 00 7740, Centeon Pharma GmbH, Marburg, Germany) o/n at RT. After 3 washes in TBS/Tw buffer, the membrane was incubated with HRP conjugated rabbit anti mouse IgG (cat.no. PO0260, Dako A/S, Copenhagen, Denmark), diluted 2.500 fold in TBS/Tw, 1 mM EDTA with 100 µg human IgG/mL for 2 h at RT. Finally, the membrane was washed 5 times in TBS/Tw and developed with Pierce's chemiluminescence substrate (SuperSignal™, cat.no. 34080, Pierce, Rockford, Ill.) on photographic films (Kodak, N.Y.).

Example 7
Analysis of rMBL by Gel Permation Chromatography

Gel permeation chromatography of purified rMBL or culture medium containing rMBL was performed on a Superose-6 column (Superose 6™ HR 10/30, cat.no. 17-0537-01, Pharmacia) equilibrated in 5 mM EDTA, TBS, 0.01% (v/v) Tween-20 [pH 7.4]. A sample volume of 100 µL (corresponding to 100 ng of rMBL or natural MBL) was passed over the column with a flow rate of 0.5 mL/min. Fractions were collected 5 mL post sample injection in volumes of 250 µL. The fractions were diluted 2 fold in TBS/Tw,10 mM EDTA and analysed by a time-resolved immunofluorometric assay (TRIFMA) as described in Example 8.

Example 8
Analysis of rMBL by a Time-Resolved Immunofluorometic assay (TRIFMA)

Flourosorp™ microtitre plates (cat.no. 437958, Nunc, Kamstrup, Denmark) were coated o/n with 100 µL (per well) of MAb 131-1 anti-MBL (Statens Serum institut, Copenhagen, Denmark) at 5 µg/mL PBS and washed trice in TBS/Tw. A standard serum with a known MBL concentration (3.0 µg MBL/mL) was diluted 20 fold in 10 mM EDTA, TBS/Tw and used as such as well as in further 5-fold dilutions with duplicate wells, each receiving 100 µL of the dilution. Three control sera, one with a high conc. of MBL (1.2 µg MBL/mL), one with a medium concentration of MBL (250 ng MBL/mL), and one with a low concentration of MBL (50 ng MBL/mL), were applied diluted 20 fold in TBS/Tw/EDTA. An MBL deficient serum was likewise diluted 20 fold and added to the plate as a negative control. Culture supernatants, either FBS containing or serum-free, were typically diluted 20 and 100 fold. After o/n incubation, the plate was washed trice in TBS/Tw and each well received 100 µL of $Eu^{3+}$ labelled MAb 131-1 anti-MBL at 125 ng/mL 25 µM EDTA,TBS/Tw. Labelled antibody was prepared essentially according to Wallac's protocol (Wallac, Turku, Finland). Development and measurement of bound europium was carried out by standard procedures for time resolved immunofluorometry as described elsewhere (Hemmila et al., 1993).

REFERENCES

Davies, E. J., Snowden, N., Hillarby, M. C., Carthy, D., Grennan, D. M., Thomson, W. & W. E. Oliter (1995) Mannose-binding protein gene polymorphism in systemic lupus erythematosus. *Arthritis. Rheum.* 38:110–114.

Drickamer, K., J., Dordal, M. S. & L. Reynolds (1986) Mannose-binding proteins isolated from rat liver contain carbohydrate-recognition domains linked to collagenous tails. *J. Biol. Chem.* 261:68778–6887.

Christiansen, O. B., Kilpatrick, D. C., Souter, V., Warming, K., Thiel, S. & J. C. Jensenius (1999) Mannan-binding lectin deficiency is associated with unexplained recurrent miscarriage. *Scand. J. Immunol.* 49:193–196.

van Emmerik, L. C., Kuljper, E. J., Fijen, C. A. P., Dankert, J. & S. Thiel (1994) Binding of mannan-binding protein to various bacterial pathogens of meningitis. *Clin. Exp. Immunol.* 97:411–416.

Garred, P., Richter, C., Andersen, A. B., Madsen, H. O., Mtoni, I., Svejgaard, A. & J. Shao (1997a) Mannan-binding lectin in the sub-saharan HIV and tuberculosis epidemics. *Scand. J. Immunol.* 46:204–208

Garred, P. Madsen, H. O. Balslev. U. Hofmann B., Pedersen, C., Gerstoft, J. & A. Svejgaard (1997b) Susceptibility to HIV infection and progression of AIDS in relation to variant alleles of mannose-binding lectin. *Lancet* 349:236–240.

Guo, N., Mogues, T., Weremowicz, S., Morton, C. C. & K. N. Sastry (1998) The human ortholog of rhesus mannose-binding protein-A gene is an expressed pseudogene that focalizes to chromosome 10. *Mamm. Genome* 9:246–249.

Hanahan, D. (1983) Studies on transformation of Escherichia cell with plasmids. *J. Mol. Biol.* 166:557–580.

Hartshom, K. L., Sastry, K., Brown, D., White, M. R., Okarma, T. B., Lee, Y. -M. & A. I. Tauber (1993) Conglutinin acts as an opsonin for influenza A viruses. *J. Immunol.* 151:626–6273.

Haurum, J., Thiel, S., Jones, I. M., Fischer, P., Laursen, S. B, & J. C. Jensenius (1993) Complement activation upon binding of mannan-binding protein to HIV envelope glycoporteins. AIDS 7:1307–1313.

Hemmila, I. Mukkala V. M., Latva, M. & P. Klilholma (1993) Di- and tetracarboxylate derivatives of pyridines, bipyridines and terpyridines as luminogenic reagents for time-resolved fluorometric determination of terbium and dysprosium. *J. Biochem. Biophys. Methods.* 26:283–290.

Holmskov, U., Holt, P., Raid, K. B. M., Willis, A. C., Teisner, B. & J. C. Jensenius (1993a) Purification and characterization of bovine mannan-binding protein. *Glycobiology* 3.147–153.

Holmskov. U. Malhotra, R., Sim, R. B. & J. C. Jensenius (1994) Collectins: collage-nous C-type lectins of the innate immune defense system. *Immunol. Today* 15:67–74.

Huang, Y., Kong, Y., Wang, Y., Qi, G. & C. Lu (1996) Stable expression of anti-HPV 16 E7-ribozyme in CV-1 cell lines. *Chin. J. Biotechnol.* 12:215–20.

lobst, S. T., Wornald, M. R., Weis, W. I., Dwek, R. A. & K. Drickamer (1994) Binding of sugar ligands to Ca(2+)-dependent animal lectins. I. Analysis of mannose binding by site-directed mutagenesis and NMR *J. Biol. Chem.* 269:15505–15511.

lp, W. K., Chan, S. Y., Lau, C. S. & Y. L. lau (1998) Association of systemic lupus erythematosus with promoter polymorphisms of mannose-binding lectin gene. *Arthritis Rheum* 41:1663–1668.

Janeway, C. A., Travers, P., Walport, M. & J. D. Capra (1999) *Immunobiology* (4th ed.). Churchill Livingston, Edinburg, 634 pp.

Ji, Y.-H., Fujita, T., Hatsuse, H., Takahashi, A., Matsushita, M. & M. Kawakami (1993) Activation of the C4 and C2 components of complement by a proteinase in serum bactericidal factor, ra-reactive factor. *J. Immunol.* 150:571–578.

Kawai, T. Suzuki. Y. Eda. S., Ohtani. K., Kase, T., Sakamoto, T., Uemura, H. & N. Wakamlya (1998) Molecular and biological characterization of rabbit mannan-binding protein. *Glycobiology* 8:237–244.

Kawasaki. T., Etoh, R. & I. Yamashina (1978) Isolation and characterization of a mannan-binding protein from rabbit liver. *Biochem. Biophys. Res. Comm.* 3:1018–1024.

Kilpatrick, D. C. (1997) Mannan binding protein is sera positive for rheumatoid factor. *Br. J. Rheumatol.* 36:207–209.

Kuhlman, M., Joiner, K. & R. A. B. Ezekowitz (1989) The human mannose-binding protein function as an opsonin. *J. Exp. Med.* 169:1733–1745.

Kurata, H. Cheng, H. M., Kozutsumi, Y., Yokota, Y. & T. Kawasaki (1993) Role of the collagen-like domain of the human serum mannan-binding protein in the activation of complement and the secretion of this lectin. *Biochem. Biophys. Res. Comm.* 191:1204–1210.

Kurate, H., Sannoh, T., Kozutsumi, Y., Yokota, Y. & T. Kawasaki (1994) Structure and function of mannan-binding proteins isolated from human liver and serum. *J Biochem.* 115:1148–1154.

Lau. Y. L. Lau, C. S., Chan, S. Y. Karlberg, J. & M. W. Turner (1996) Mannose-binding protein in Chinese patients with systemic lupus erythematosus. *Arthritis Rheum* 39:706–708.

Laursen, S. B., Hedernand, J. E., Thiel, S., Willis, A. C., Skriver, E., Madsen, P. S. & J. C. Jensenius (1995) Collectin in a n n-mammalian species; isolation and characterization of mannan-binding protein (MBP) from chicken serum. *Glycobiology* 5:553–561.

Laursen, S. B., Dalgaard, T. S., Thiel, S., Lim, B. L., Jensen, T. V., Juul-Madsen, H. R., Takahashi, A., Hamana, T., Kawakami, M. & J. C. Jensenius (1998) Cloning and sequencing of a cDNA encoding chicken mannan-binding lectin (MBL) and comparison with mammalian analogues. *Immunology* 93:421–430.

Law, S. K. A. & K. R. M. Reid (1995) Complement, IRL Press, Oxford.

Lipscombe, R. J., Lau, Y. L., Levinsky, R. J., Sumlya, M., Summerfield, J. A. & M. W. Turner (1992a) identical point mutation leading to low levels of mannose binding protein and poor C3b mediated opsonisation in Chinese and Caucasian populations. *Immunol. Lett.* 32:253–257.

Lipscombe, R. J., Sumlya, M., Hill, A. V., Lau, Y. L., Levinsky, R. J., Summerfield, J. A. & M. W. Turner (1992b) High frequencies in African and non-African populations of independent mutations in the mannose binding protein gene. *Hum. Mol. Genet.* 1:709–715.

Lipscombe, R. J., Sumiya, M., Summerfield, J. A. & M. W. Turner (1995) Distinct physicochemical characteristics of human mannose-binding protein expressed by individuals of differing genotype. *Immunology* 85:660–667.

Lu, J. Thiel, S., Wiedernann, H., Timpi, R. & K. B. M. Reid (1990) Binding of the pentamer/hexamer forms of mannan-binding protein to zymosan activates the proenzymes $C1r_2C1s_2$ complex, of the classical pathway of complement without involvement of C1q. *J. Immunol.* 144:2287–2294.

Ma, Y. Yokota, Y., Kozutsumi, Y. & T. Kawasaki (1996) Structural and functional roles of the amino-terminal region and collagen-like domain of human serum mannan-binding protein. *Biochem. Mol. Biol. Int.* 40:965–974.

Ma, Y., H. Shida & T. Kawasaki (1997) Functional expression of human mannan-binding proteins (MBPs) in human hepatoma cell lines infected by recombinant vaccinia virus: post-translational modification, molecular assembly, and differentiation of serum an liver MBP. *J. Biochem.* (Toyo) 122: 610–818.

Ma, Y., Uemura, K., Oka, S., Kozutsumi, Y., Kawasaki, N. & T. Kawasaki (1999) Antitumor activity of mannan-binding protein in vivo as revealed by a virus expression system: mannan-binding protein-dependent cell-mediated cytotoxicity. *PNAS* 96:371–375.

Madsen. H. O., Garred, P., Kurtzhals, J. A., Lamm, L. U. Ryder, L. P., Thiel, S. & A Svejgaard (1994) A new frequent allele is the missing link in the structural polymorphism of the human mannan-binding protein. *Immunogenetics* 40:37–44.

Madsen, H. O., Garred, P., Thiel, S., Kurtzhals, J. A., Lamm, L. U., Ryder, L. P., & A. Svejgaard (1995) Interplay between promoter and structural gene variants control basal serum level of mannan-binding protein. *J. Immunol.* 155:3013–3020.

Malhotra, R., Haurum. J. S., Thiel. S. & R. B. Sim (1994) Binding of human collectins (SP-A and MBP) to influenza virus. *Biochem. J.* 304:455–461.

Matsushita. M. & T. Fujita (1992a) Activation of the classical complement pathway by mannose-binding protein in association with a novel C1s-like protease. *J. Exp. Med.* 176:1497–1502.

Matsushita, M., Ezekowitz, R. A. B. & T. Fujita (1995a) The Gly-54→Asp allelic form of human mannose-binding protein (MBP) fails to bind MBL-associated serine protease. *Biochem. J.* 311:1021–1023.

Mizuno. Y. Kozutmi, Y., Kawasaki, T. & I. Yamashina (1981) isolation and characterization of a mannan-binding protein from rat liver. *J. Biol. Chem.* 256:4247–4252.

Mogues, T., Ota, T., Tauber, A. I. & K. N. Sastry (1996) Characterization of two mannose-binding protein cDNAs from rhesus monkey (*Maraca mulatta*): structure and evolutionary implications. *Glycobiology* 6:543–550.

Makrides, S. C., "Components of vectors for Gene Transfer and Expression in Mammalian Cells"

Nakajima, T. & C. E. Ballou (1974) Characterization of the carbohydrate fragments obtained from *Sacoharomyces cerevisiae* mannan by alkaline degradation. J. Biol. Chem. 249:7679–7684.

Ng, K. K., Drickamer, K. & W. I. Weis (1996) Structural analysis of monosaccharide recognition by rat liver mannose-binding protein. *J. Biol. Chem.* 271:663–674.

Nielsen, S. L., Andersen, P. L., Koch, C., Jensenius, J. C. & S. Thiel (1995) The level of the serum opsonin, mannan-binding protein in HIV-1 antibody-positive patients. *Clin. Exp. Med.* 100:219–222.

Ohta, M., Okada. M., Yamashina. I. & T. Kawasaki (1989) The mechanism of carbohydrate-mediated complement activation by the serum mannan-binding protein. *J. Biol. Chem.* 265:1980–1984.

Ohtani, K., Suzuki, Y., Eda, S., Kawai, T., Kase, T., Keshi, H., Sakai, Y., Vamamoto, S., Sakamoto, T. & N. Wakamiya (1999) High-level and effective production of human mannan-binding lectin (MBL) in Chinese hamster ovary (CHO) cells. *J. Immunol. Methods.* 222:135–44.

Oka. S., Ikeda. K. Kawasaki, T. & I. Yamashina (1985) Isolation and characterization of mannan-binding proteins from chicken liver. *Arch. Biochem. Biophys.* 241:95–106.

Oka, S., Ikeda, K., Kawasaki, T. & I. Yamashina (1988) Isolation and characterization of two distinct mannan-binding proteins from rat serum. *Arch. Biochem. Biophys.* 260:257–266.

Pastinen, T., Litsola, K., Niinl, P., Salminen, M. & A. -C. Syvänen (1998) Contribution of the CCR5 and MBL genes to susceptibility to HIV type 1 infection in the Finnish population. *AIDS Res. Hum. Retroviruses* 14:695–698.

Reddy, P. S. & R. B. Corley (1998) Assembly, sorting, and exit of oligomeric proteins from the endoplasmic reticulum. *Bioessays* 20:546–554.

Sastry, K., Herman, G. A., Day, L., Deignan, E., Bruns, G., Moron, C. C. & R. A. B. Ezekowitz (1989) The human mannose-binding protein gene. *J. Exp. Med.* 170:1175–1189.

Sato, T., Endo, Y., Matsushita, M. & T. Fujita (1994) Molecular characterization of a novel serine protease involved in activation of the complement system by mannose-binding protein. *Int. Immunol.* 6:665–669.

Schweinle, J. E. Nishiyasu, M. Ding. T. Q. Sastry. K. Gillies, S. D. & R. A. B. Ezekowitz (1993) Truncated forms of mannose-binding protein multimerize and bind to mannose-rich *salmonella montevideo* but fail to activate complement in vitro. *J. Biol. Chem.* 268:364–370.

Sheriff. S., Chang, C. Y. & R. A. B. Ezekowitz (1994) Human mannose-binding protein carbohydrate recognition domain trimerizes through a triple α-helical coiled-cell. *Structural biol.* 1:789–794.

Soothill, J. F. & B. A. Harvey (1976) Defective opsonization. A common immunity deficiency. *Arch. Dis. Child.* 51:91–99.

Stover, C. M., Thiel, S., Thelen, M., Lynch, N. J., Vorup-Jensen, T., Jensenius, J. C. & W. J. Schwaeble (1999) Two constituents of the initiation complex of the mannan-binding lectin activation pathway of complement are encoded by a single structural gene. *J. Immunol.* 162:3481–3490.

Sumiya, S., Super, M., Tabona, P., Levinsky, R. J. Arai, T., Turner. M. W. & J. A. Summerfield (1991) Molecular basis of opsonic defect in immunodeficient children. *Lancet* 337:1569–1570.

Super, M., Thiel, S., Lu, J. Levinsky, R. J. & M. W. Turner (1989) Association of low levels of mannan-binding protein with a common defect opsonisation. *Lancet* 11:1236–1239.

Super, M. Gillies. S. D., Foley, S., Sastry, K., Schweinle, J. E., Silverman, V. J. and R. A. B. Ezekowitz (1992) Distinct and overlapping functions of allelic forms for human mannose-binding protein. *Nature Genet.* 2:50–55.

Tabona, P., Mellor, A. & J. A. Summerfield (1995) Mannose binding protein is involved in first-line host defence: evidence from transgenic mice. *Immunology* 85:153–159.

Takada, F., Takayama, Y., Hatsuse, H. & M. Kawakami (1993) A new member of the C1s family of complement proteins found in a bactericidal factor, ra-reactive factor, in human serum. *Biochem. Biophys. Res. Commun.* 196:1003–1009.

Takayama, Y., F. Takada, Takahashi, A. and M. Kawakami (1994) A 100 kDa protein in the C4-activating component of ra-reactive factor is a new serine protease having module organization similar to C1r and C1s. *J. Immunol.* 152:2308–2316.

Tan, F. K. & F. C. Arnett (1998) The genetics of lupus. *Cur. Opin. Rheumatol.* 10:389–408.

Taylor, M. E., Brickell, P. M. Craig, R. K. & J. A. Summerfield (1969) Structure and evolutionary origin of the gene encoding a human serum mannose-binding protein. *Biochem. J.* 262:763–771.

Thiel, S., Vorup-Jensen, T., Stover, C. M., Schwaeble, W., Laursen, S. B. Poulsen. K., Willis, A. C., Eggleton, P., Hansen, S., Holmskov, U., Raid, K. B. & J. C. Jensenius (1997). A second serine protease associated with mannan-binding lectin that activates complement. *Nature* 386:508–510.

Turner, M. W. (1996) Mannose-binding lectin: the pluripotent molecule of the innate immune system. *Immunol. Today* 17:532–540.

Valdimarsson, H., Stefansson, M., Vikingsdottir, T., Arason, G. J. Koch, C., Thiel, S. & J. C. Jensenius (1998) Reconstitution of opsonizing activity by infusion of mannan-binding lectin (MBL) to MBL-deficient humans. *Scand. J. Immunol.* 48:116–23.

Vorup-Jensen, T., Jensenius, J. C. & S. Thiel (1998) MASP-2, the C3 convertase generating protease of the MBLectin complement activating pathway. *Immunobiology* 199:340–357.

Voss, T., Maichers, K., Scheirie, G. & K. P. Shäfer (1991) Structural comparison of recombinant pulmonary surfactant protein SP-A derived from two human coding sequences: implications for the chain composition of natural human SP-A. *Am. J. Respir. Cell Mol. Biol.* 4:88–94.

Weis, W. I., Drickamer, K. & W. A. Hendrickson (1992) Structure of a C-type mannose-binding protein complexed with an oligosaccharide. *Nature* 360:127–134.

Weis, W. I. & K. Drickamer (1994) Trimeric structure of a C-type mannose-binding protein. *Structure* 2:1227–1240.

What is claimed is:

1. A process of producing a purified recombinant human mannan binding lectin (MBL) composition which is free of monomers of the 96 kDa MBL subunit which comprises providing a starting recombinant human MBL composition comprising both (a) monomers of the 96 kDa MBL subunit and (b) at least one oligomer selected from the group consisting of dimers, trimers, tetramers, pentamers and hexamers of said 96 kDa MBL subunit, wherein said 96 kDa subunit comprises the polypeptide of SEQ ID NO:1 separating (b) from (a) by subjecting the composition to affinity chromatography using a carbohydrate-derivatized matrix having affinity for at least one oligomer of (b) and which substantially lacks affinity for said monomers of (a), and thereby obtaining a purified composition which comprises at least one oligomer of (b) and which is without any detectable amount of said monomer (a) of said 96 kDa MBL subunit.

2. The process of claim 1 wherein said starting recombinant MBL composition is obtained by preparing an expression construct encoding the human MBL polypeptide of SEQ ID NO. 1, transforming a host cell culture with the construct, and cultivating the host cell culture, thereby obtaining expression and secretion of the polypeptide into the culture medium, said starting composition being said MBL-containing culture medium or an MBL-containing composition derived therefrom.

3. The process according to claim 2, wherein the gene expression construct comprises a cDNA sequence encoding a MBL subunit.

4. The process according to claim 2, wherein the host cell culture is a mammalian host cell culture.

5. The process of claim 1, wherein said derivatized matrix has no detectable affinity for dimers of 96 kDa MBL subunits.

6. The process of claim 5, wherein said derivatized matrix has no detectable affinity for trimers of 96 kDa MBL subunits.

7. The process of claim 1, wherein said derivatized matrix was obtained by derivatizing an underivatized matrix, and the underivatized matrix has no detectable affinity for monomers of the 96 kDa MBL subunits.

8. The process of claim 1 wherein said derivatized matrix was obtained by derivatizing an underivatized matrix, and the underivatized matrix has substantially no affinity for dimers of 96 kDa MBL subunits.

9. The process of claim 8 wherein said derivatized matrix was obtained by derivatizing an underivatized matrix, and the underivatized matrix has substantially no affinity for trimers of 96 kDa MBL subunits.

10. The process of claim 7 wherein the underivatized matrix has no detectable affinity for either dimers or trimers of 96 kDa MBL subunits.

11. The process of claim 1 wherein said starting composition comprises dimers of said 96 kDa MBL subunit, said carbohydrate-derivatized matrix also substantially lacks affinity for said dimers, and wherein the purified composition is without any detectable amount of such dimers.

12. A process of producing a purified recombinant human mannan binding lectin (MBL) compositions which is enriched for at least one higher oligomer selected from the group consisting of tetramers, pentamers and hexamers of the 96 kDa MBL subunits, which comprises providing a starting recombinant human MBL composition comprising both (a) monomers of the 96 kDa MBL subunit and (b) at least one higher oligomer selected from the group consisting of tetramers, pentamers and hexamers of said subunit, separating (b) from (a) by subjecting the composition to affinity chromatography using a carbohydrate-derivatized matrix which has a higher affinity for (b) than for (a), thereby obtaining a purified composition wherein the ratio of (1) the sum of the tetramers, pentamers and hexamers of the 96 kDa MBL subunit, to (2) the monomers of the 96 kDa MBL subunit, is at least 5:1.

13. A process of producing a purified recombinant human mannan binding lectin (MBL) composition, which is enriched for at least one higher oligomer selected from the group consisting of tetramers, pentamers and hexamers of the 96 kDa MBL subunits, which comprises providing a starting recombinant human MBL composition comprising both (a) monomers and/or dimers of the 96 kDa MBL subunit and (b) at least one higher oligomer selected from the group consisting of, tetramers, pentamers and hexamers of said subunit, separating (b) from (a) by subjecting the composition to affinity chromatography using a carbohydrate-derivatized matrix which has a higher affinity for (b) than for (a), thereby obtaining a purified composition wherein the ratio of (1) the sum of the tetramers, pentamers and hexamers of the 96 kDa MBL subunit, to (2) the sum of the monomers and dimers of the 96 kDa MBL subunit, is at least 2:1.

14. The process of claim 13 wherein said ratio is at least 5:1.

15. A process of producing a purified recombinant human mannan binding lectin (MBL) composition which is enriched for hither oligomers, selected from the group consisting of tetramers, pentamers, and hexamers of the 96 kDa MBL subunit, which comprises providing a starting recombinant human MBL composition which comprises (a) monomers and/or dimers of the 96 kDa MBL subunit, and (b) said higher oligomers, of said subunit, subjecting the starting composition to affinity chromatography using a carbohydrate-derivatized matrix which has a higher affinity for at least one of said oligomers of (b) than for said monomers and/or dimers thereof, thereby obtaining a purified composition enriched, relative to said starting composition, for said oligomers of (b), and in which more than 50% of the MBL is in the form of said oligomers of (b).

16. The process of claim 1 in which the carbohydrate is a hexose.

17. The process of claim 1 in which the carbohydrate is mannose.

18. The process of claim 1 wherein said carbohydrate-derivatized matrix is obtained by conjugating a carbohydrate having affinity for at least one of said oligomers of the 96 kDa MBL subunit, to a matrix which is carbohydrate-free.

19. The process of claim 18 in which the underivatized matrix has substantially no affinity for the 96 kDa MBL subunit.

20. The process of claim 1 in which the matrix is a carbohydrate-derivatized polyvinyl polymer matrix.

21. The process of claim 17 in which the matrix is a mannose-derivatized polyvinyl polymer matrix.

22. The process of 15 in which more than 60% of the MBL in the purified composition is in the form of said oligomers of (b).

23. The process of 15 in which more than 70% of the MBL in the purified composition is in the form of said oligomers of (b).

24. The process of 15 in which more than 80% of the MBL in the purified composition is in the form of said oligomers of (b).

25. The process of 15 in which more than 90% of the MBL in the purified composition is in the form of said oligomers of (b).

26. The process of 15 in which more than 95% of the MBL in the purified composition is in the form of said oligomers of (b).

27. A process of producing a purified recombinant human mannan binding lectin (MBL) composition which is free of monomers of the 96 kDa MBL subunit which comprises providing a starting recombinant human MBL composition comprising both (a) monomers of the 96 kDa MBL subunit and (b) at least one oligomer selected from the group consisting of dimers, trimers, tetramers, pentamers and hexamers of said 96 kDa MBL subunit, separating (b) from (a) by subjecting the composition to affinity chromatography using a carbohydrate-derivatized matrix having affinity for at least one oligomer of (b) and which substantially lacks affinity for said monomers of (a), and thereby obtaining a purified composition which comprises at least one oligomer of (b) and which is without any detectable amount of said monomer (a) of said 96 kDa MBL subunit wherein said starting recombinant MBL composition is obtained by providing a nonhuman transgenic mammal whose cells comprise an expression construct encoding the human MBL polypeptide of SEQ ID NO:1, producing said polypeptide in said mammal, and recovering said starting MBL composition from at least one body tissue or body fluid of said mammal.

28. The method of claim 1, further comprising eluting said purified composition from said derivatized matrix.

29. The process according to claim 28 wherein, in the eluted purified composition the ratio of (a) the sum of the tetramers, pentamers and hexamers of 96 kDa MBL subunits to (b) the sum of monomers and dimers of 96 kDa MBL subunits is at least 2:1.

30. The process according to claim 28 wherein, in the eluted purified composition the ratio of (a) the sum of the tetramers, pentamers and hexamers of 96 kDa MBL subunits to (b) the sum of monomers and dimers of 96 kDa MBL subunits is at least 5:1.

* * * * *